United States Patent [19]

Hill et al.

[11] 4,237,912

[45] Dec. 9, 1980

[54] WASHING, PASTEURIZING AND DISINFECTING APPARATUS

[75] Inventors: Eleanor S. Hill; William J. Hill; Ralph C. Hill, all of Mercer Island, Wash.

[73] Assignee: H & R Incorporated, Seattle, Wash.

[21] Appl. No.: 958,604

[22] Filed: Nov. 8, 1978

[51] Int. Cl.³ .......................... B08B 3/06; B08B 9/00; B08B 11/02
[52] U.S. Cl. .................................... 134/57 R; 134/75; 134/112; 134/158; 134/169 R
[58] Field of Search ....... 134/57 R, 95, 112, 157–158, 134/166 R, 169 R, 170, 161; 68/174

[56] References Cited

U.S. PATENT DOCUMENTS

| | | | |
|---|---|---|---|
| 2,173,564 | 9/1939 | Osuch | 134/158 X |
| 3,007,478 | 11/1961 | Leonhardt et al. | 134/57 R |
| 3,690,333 | 9/1972 | Kierner | 134/95 |
| 3,739,791 | 6/1973 | Fry et al. | 134/157 |
| 3,881,503 | 5/1975 | Fox et al. | 134/57 R |
| 3,884,265 | 5/1975 | Fry et al. | 134/157 X |
| 3,893,843 | 7/1975 | Fry et al. | 134/10 |
| 3,974,843 | 8/1976 | Aubert | 134/95 |
| 3,991,779 | 11/1976 | Saurenman | 134/57 R |

*Primary Examiner*—Robert L. Bleutge
*Attorney, Agent, or Firm*—Hughes, Barnard & Cassidy

[57] ABSTRACT

A cleaning tub having therein a holding basket mounted for rotation about a vertical axis. The basket has a lower section with circumferentially aligned holding and partition members to contain tubular-like members to be cleaned in circumferential alignment. There is also an upper section having radial partitions to contain other objects to be cleaned. During a first washing and rinsing cycle, the basket is caused to oscillate throughout the filling period, the washing period, the emptying period, and also through a final "shake-off" period. There is also a transfer tub to hold either a pasteurizing liquid (i.e. hot water) or a disinfect liquid. Subsequent to the washing cycle, the liquid in the transfer tub can be moved over to the cleaning tub either to pasteurize or disinfect the articles in the basket. Heat control means are provided to bring the transfer liquid to the proper temperature in the transfer tub, and also to maintain this proper temperature in the cleaning tub.

40 Claims, 15 Drawing Figures

FIG. 3
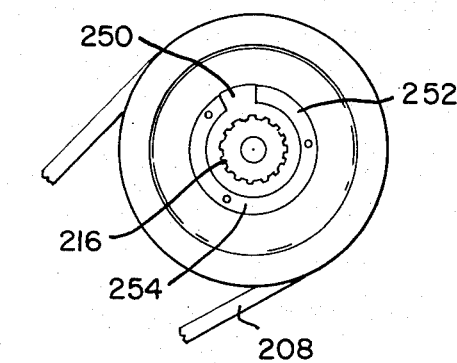
FIG. 3A
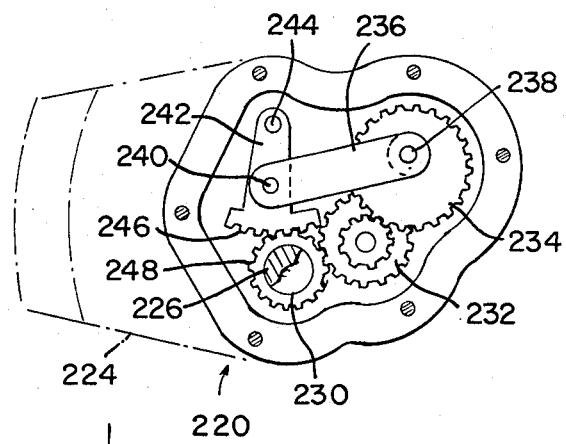
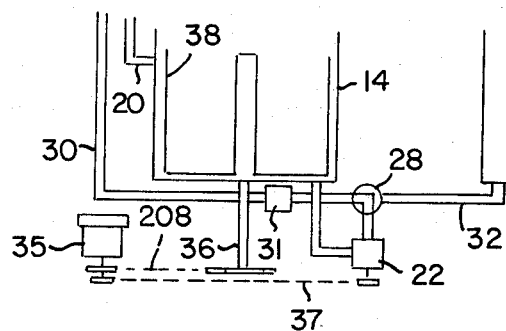
FIG. 4
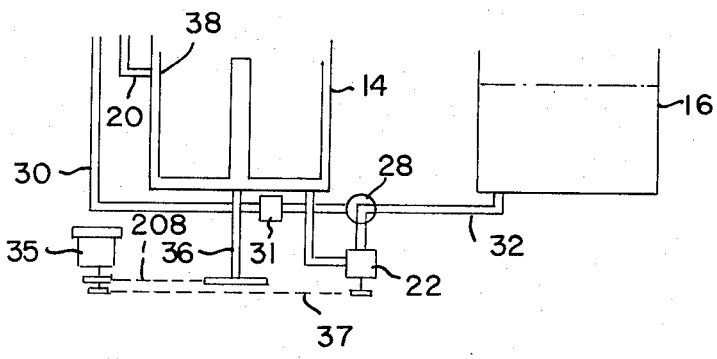
FIG. 5
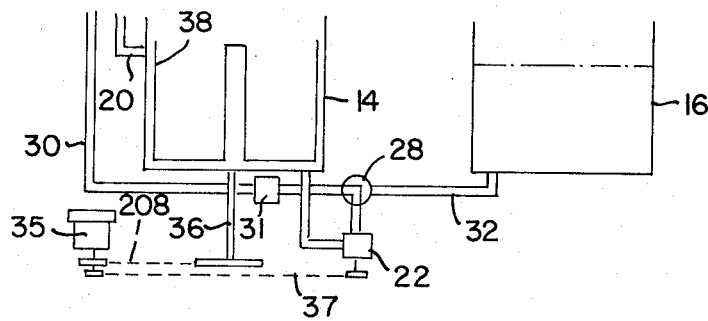
FIG. 6

WASHING, PASTEURIZING AND DISINFECTING APPARATUS

BACKGROUND OF THE INVENTION

The present invention relates to an apparatus and method for cleaning hospital related equipment, particularly equipment used in anesthetizing patients or for inhalation therapy.

The type of equipment used for anesthetizing or inhalation therapy is made up of a variety of tubes, breathing bags, fittings, etc. Since these components are very susceptible to contamination, it is particularly important that there be provided means for cleaning these components effectively and reliably. This is generally accomplished by first washing the components to remove as much foreign material as possible, and then following the washing with either a sterilizing or disinfecting process. The sterilizing is accomplished by immersing the components in a hot liquid (i.e. water at a temperature of about 160°) for a suitable period of time (e.g. 25 to 35 minutes). Quite often, instead of pasteurizing the components, the sterilization is accomplished by immersing the components in a disinfecting solution which may or may not be at an elevated temperature.

U.S. Pat. No. 3,739,791, Fry et al, discloses an apparatus particularly adapted for washing and disinfecting articles used in anestheseology and inhalation therapy. In that apparatus, there is a cleaning tub having therein a containing basket mounted for rotation about a vertical axis. There is also a transfer tub to contain a disinfectant liquid. The articles to be cleaned are placed in the basket with the tubular articles being aligned in a somewhat spiral configuration so that the open ends of these tubular members are at the outer portion of the basket, and the tubular members slant radially outwardly toward their open ends. This spiral configuration of the tubular components is intended to aid in the removal of the liquid during the rapid spinning of the basket.

During the washing cycle, the tub is first filled with wash water, and then the basket is agitated (oscillated angularly about its axis of rotation) during a wash period. After the wash period, the wash water is drained from the tub, and the basket is spun at a relatively high speed to remove droplets of wash water from the components being cleaned. Then the components are rinsed with clear water, following substantially the same sequence as during the above-described washing process.

Subsequent to the washing process a disinfect liquid in the transfer tub is pumped into the cleaning tub to a level to totally immerse the components in the disinfect liquid. Then the basket is oscillated for a period of time, with the equipment immersed in the disinfect liquid, after which the disinfect liquid is pumped back into the transfer tub, and the basket spun at high speeds to remove remaining droplets of the disinfect liquid. This can be followed by one or more rinsing cycles with clear water. (This same subject matter is disclosed in two patents resulting from divisional applications of the application which resulted in the above noted Fry et al patent. The two other patents are U.S. Pat. Nos. 3,884,265 and 3,893,843.)

The following patents were noted in a patentability search conducted on the concept of the present invention. These are not considered to be particularly relevant art to the present invention, but these are noted herein to insure that the applicants are complying with their duty to disclose all material which might be of possible relevance.

U.S. Pat. No. 3,690,333, Kierner, discloses a machine for cleaning small parts in which a vacuum pump is used to insure that all liquid is removed from the washing area.

U.S. Pat. No. 3,974,843, Aubert, discloses a washing machine particularly adapted for dental instruments and equipment for making dental prostheses. This patent is directed particularly toward a propeller which produces a gyratory circulation of the liquid in the tank to cause the cylinder to rotate, and also to cause pulsations and vibrations to create turbulence in the tank.

U.S. Pat. No. 3,991,779, Saurenman, discloses medical equipment cleaning apparatus in the form of a side loading washing machine. This patent is concerned particularly with the means for sensing and regulating the water which is directed into the apparatus.

SUMMARY OF THE INVENTION

The washing apparatus of the present invention is particularly adapted to clean elongate hollow articles, such as tubes and other equipment used in anesthetizing and inhalation therapy. The apparatus comprises a housing structure, and a tub mounted in the housing structure and adapted to contain a cleaning liquid. In the tub is a container adapted to carry the articles which are to be cleaned. This container is mounted for rotation about a generally vertical axis of rotation.

There is means to fill the tub with a cleaning liquid, and also means to empty the cleaning liquid from the tub. Power means is operatively connected to the container to cause the container to oscillate angularly about the axis of rotation. Positioning means are provided in the container and arranged to engage and maintain the elongate articles in the container in circumferential alignment with the center of rotation of the container.

To operate the apparatus, there is control means to cause the filling means to direct liquid into the tub, and also causes the emptying means to remove the cleaning liquid from the tub. The control means is arranged to activate the power means to oscillate the container during a time period when said tub is filled with the liquid to a cleaning level, and also to oscillate the tub during a period after the cleaning liquid has been removed from the tub. Thus, subsequent to the cleaning liquid being removed from the tub, the articles in the container are oscillated angularly to remove at least a portion of liquid remaining on the articles after the tub is emptied of the cleaning liquid.

In the preferred form, the positioning means in the container comprises at least one locating means positioned in the container, said locating means having vertically oriented and radially spaced partition means defining a plurality of circumferentially aligned, radially spaced locating areas to receive the articles in circumferential alignment. Also, in the preferred form, the positioning means comprises at least one clamping means, comprising a plurality of radially spaced clamping members adapted to engage the articles. Each of the clamping members defines a circumferentially aligned clamping area in which the articles are located to be clamped in circumferential alignment. Specifically, the locating means comprises at least one locating member having a base portion and a plurality of upstanding rod members, with adjacent rod members defining the locating areas. Further, the specific form of the clamping means comprises a base member, with each of the clamping elements comprising a strap member connected to the base member and adapted to define a closed loop.

The container has at least one horizontal partition member dividing the container into an upper section and a lower section. The positioning means is located in the lower section so that the difficult to clean elongate articles are located in the lower section, and other articles to be cleaned are able to be placed in the upper section. The control means is so arranged as to cause the power means to oscillate the container during a time period when the filling means is directing cleaning liquid into the tub. Thus, when the tub is partially filled with cleaning liquid, the container is oscillating in the tub to cause a cleaning action of the articles in the lower section of the container. In like manner, the control means is arranged to cause the power means to oscillate the container during a period when the emptying means is emptying the cleaning liquid from the tub. Thus, also during the time period when emptying of the tub begins to a time when emptying of the tub is partially completed, said container is caused to oscilate to impart a cleaning action to the articles in the lower section of the container.

Desirably, the horizontal partition member comprises a plate and a resilient wire member positioned at a peripheral portion of the plate, with the container having a plurality of vertically spaced groove means to receive the wire member. Thus, the wire member can be sprung inwardly to provide clearance for the partition member to be placed in the container, and sprung outwardly to engage selected groove means to locate the partition member at a desired vertical location. The wire member has a plurality of brackets connecting the wire member to the plate. The brackets are movable relative to the plate, so that the wire member can be sprung inwardly and outwardly while the brackets maintain engagement with the plate. Preferably, the plate is provided with a plurality of grooves, each groove arranged to accommodate a related one of the brackets as the wire member is sprung inwardly.

The wire member has a peripheral portion extending circumferentially around the plate, and two radially inwardly extending arm portions. The two arm portions are spaced moderately from one another, so that the arm portions can be grasped and pulled toward one another to cause the wire member to be sprung inwardly. The arm portions are positioned below the plate, with the plate being provided with a generally circumferentially aligned slot extending beyond the arm members. Thus, access through the slot can be obtained to grasp the arm members to move the arm members toward one another.

The container has a hub portion and a peripheral portion. There are a plurality of interior vertical mounting posts at the hub portion, and a plurality of outer circumferential posts at the peripheral portion. Pairs of inner and outer posts are radially aligned with one another. The positioning means comprises at least one positioning member having a horizontally extending base portion and two end arm portions. Each of the arm portions is adapted to engage a related one of the posts in mounting engagement, so that the positioning member can be radially aligned in the basket by one of the arm members engaging an outer post. Desirably, the groove means are formed as horizontal grooves in the outer posts to receive the peripheral wire member of the horizontal partition member.

In the preferred form, the control apparatus of the present invention comprises a liquid level switch operatively connected to the tub in a manner to be responsive to a level of cleaning liquid in the tub. The liquid level switch has a first low level position, where it activates the filling means and a motor means simultaneously, and a second high level position where the liquid level switch means deactivates the filling means. The motor means is operatively connected to the container to cause the container to oscillate. Thus, the during the filling of the tub, the container is caused to oscillate.

The control means further comprises a timer motor arranged to operate the motor means through a washing period subsequent to the filling period. The liquid level switch means is operatively connected to the timer motor to activate the timer motor at its high level position, thus causing the operation of the motor means through the washing period. The motor means has a forward operating mode, and a reverse operating mode. The apparatus is further provided with a first transmission operatively connected between the motor means and the container. The first transmission is arranged to translate rotary motion of the motor means in both its forward and reverse operating modes to oscillating motion, so that the container is caused to oscillate when the motor means is operating in either its forward mode or reverse mode.

There is a second transmission operatively connected between the motor means and the pump means. The motor means causes the pump to operate in a pump in direction when the motor is operating in its forward mode, and to cause the pump means to operate in a pump out direction when the motor means is operating in its reverse mode. The control means is arranged to operate the motor means in its forward mode during a cleaning period after said tub has been filled with cleaning liquid, and to operate the motor in its reverse mode during an emptying period subsequent to the cleaning period, so that the container continues to oscillate as the pump means is emptying the tub of the cleaning liquid.

In the preferred form, the control means comprises cam means arranged to travel through an operating cycle, and a timer motor to move the cam means through its operating cycle. There is a motor reversing switch to cause the motor means to be in its forward mode or reverse mode. There is also a motor power switch means to supply power to the motor.

The cam means has a wash position where the cam means acts through the motor reversing switch means and the motor power switch means to cause the motor to operate in its forward mode to oscillate the container and to cause the pump means to operate in its pump in mode. The cam means also has an emptying position where the cam means activates the motor reverse switch means and the power motor switch means to cause the motor means to operate in its reverse mode and thus pump out cleaning liquid from the tub while the motor means is causing the container to oscillate. Further, the cam means has a shake-dry position, where the motor power switch means is activated to cause the container to oscillate subsequent to the pump means pumping out the cleaning liquid from the tub.

The apparatus is provided with a second transfer tub to contain a second liquid medium, such as a disinfect liquid or a pasteurizing liquid. The second tub is provided with a heating means to maintain the liquid in the second tub at a desired level. Likewise, the first tub is provided with a second heating means to maintain the second liquid at a proper temperature after it has been transferred into the first tub.

The apparatus is also provided with a diverter valve having a first position to cause the pump to communicate to a discharge area, and a second position to cause the pump to communicate with the second tub. Switch means is provided to operate the switch means for the diverter valve to move into its second position, and also to operate the motor in its forward mode to cause the second liquid medium to be transferred to the first tub.

There is a second timing means arranged to determine the time period during which said second liquid medium remains in said first tub. This second timing means is operatively connected to a thermostat means so that the second timing means does not begin to operate until the thermostat senses that the temperature in the first tub has reached a predetermined level. This insures that the contact time of the second liquid medium in the first tub is measured only when the liquid medium in the first tub is at the desired temperature level. Further, there is a second liquid level switch means which activates the second timing means only when the liquid level of the second liquid medium has reached a predetermined level in the first tub.

In the method of the present invention, a container and tub are provided as indicated above. The tub is filled with a cleaning liquid, and the container is oscillated angularly after the tub has been filled. Subsequently, the cleaning liquid is removed from the tub. The container is oscillated during at least the filling period or the removing period so that there is an oscillating washing motion when the tub is partially full. In the preferred form, the tub is oscillated through both the filling and emptying periods, and the oscillation is continued after the emptying of the tub. This provides the afore-mentioned shake-dry.

Also, in the method of the present invention, the second liquid medium is transferred into the first tub so that the articles in the first tub are in contact with the second liquid medium for a predetermined contact period. The container in the first tub is caused to oscillate during both the filling and the emptying of the first tub with the second liquid medium. Subsequent to the emptying of the first tub of the second liquid medium, the container is oscillated for a further shake-dry period.

Prior to transferring the second liquid medium, the liquid medium in the second tub is heated to a predetermined level, and then transferred. In the event that the second liquid medium loses some heat in being transferred, there is a second heating step in the first tub. The contact time of the second liquid medium is delayed until the heating of the liquid brings the liquid in the first tub to the desired predetermined level.

As a further feature of the present invention, there is provided a particular means of converting a conventional clothes washing machine to accomplish the operating cycles of the present invention. In that prior art washing machine, there is a drive system comprising a drive pulley connected to a vertical drive shaft. The upper end of the drive shaft connects to a transmission which translates rotary motion to oscillating motion, and the output of the transmission is normally connected to a washing element in the machine. In the present invention, this transmission output is connected to the above described container.

There is a drive sleeve surrounding the drive shaft, and this drive sleeve is connected to the housing of the transmission. This sleeve is connected at its lower end to a brake drum of a brake assembly. A compression spring normally forces the brake drum into engagement with the brake housing, to maintain the sleeve and the transmission housing stationary.

The drive shaft is connected to the pulley through a helical thread connection, in a manner that there is relative rotational motion between the drive shaft and the pulley, the shaft translates axially relative to the pulley. The drive shaft and pulley have a pair of radially extending drive elements which permit approximately 270° rotation between the pulley and the drive shaft. When the drive shaft rotates in a first direction, where it is desired to cause oscillation at the output of the transmission, the brake drum remains in contact with its housing to maintain the sleeve and the transmission housing stationary. When the direction of the shaft is reversed, the brake drum is caused to move upwardly against the urging of a compression spring to permit the sleeve and transmission housing to rotate. An upper clutch element is also engaged to cause the entire housing to rotate. In this manner, in the conventional washing machine, the transmission output is a rotary motion which causes the container for the clothes to spin during the completion of a wash cycle.

The above-described apparatus is modified by preventing relative rotation between the drive shaft and the pulley. This is most conveniently accomplished by providing a blocking member which maintains the two radially extending drive elements of the shaft and pulley in constant contact with one another. Thus, when the rotational movement of the pulley is reversed, the drive shaft continues to act through the transmission to provide oscillating motion as the output. In this manner, the present invention quite conveniently provides for the oscillation of the container during both forward and reverse operating modes of the motor. Thus, it is possible to oscillate the container in the same manner whether the pump means (which is operated in its pump in and pump out mode by operating the motor in either forward or reverse directions) is either pumping in or pumping out.

Other features of the present invention will become apparent from the following detailed description.

BRIEF DESCRIPTION OF THE DRAWING

FIG. 3 is a view taken at line 3—3 in FIG. 2, to illustrate a portion of the drive system of the invention;

FIG. 3A is a sectional view taken along line 3A—3A to illustrate the gear transmission of the present invention;

FIG. 4 is a semi-schematic view of the apparatus of the present invention, illustrating the flow pattern of liquid during the washing and rinsing operations of a first cycle;

FIG. 5 is a view similar to FIG. 4 to illustrate the flow patterns during a pasteurzing/disinfect cycle of the present invention;

FIG. 6 is a view similar to FIGS. 4 and 5, illustrating the flow pattern during a final rinsing cycle which follows the disinfect cycle;

DESCRIPTION OF THE PREFERRED EMBODIMENT

Introduction

Figure 1:
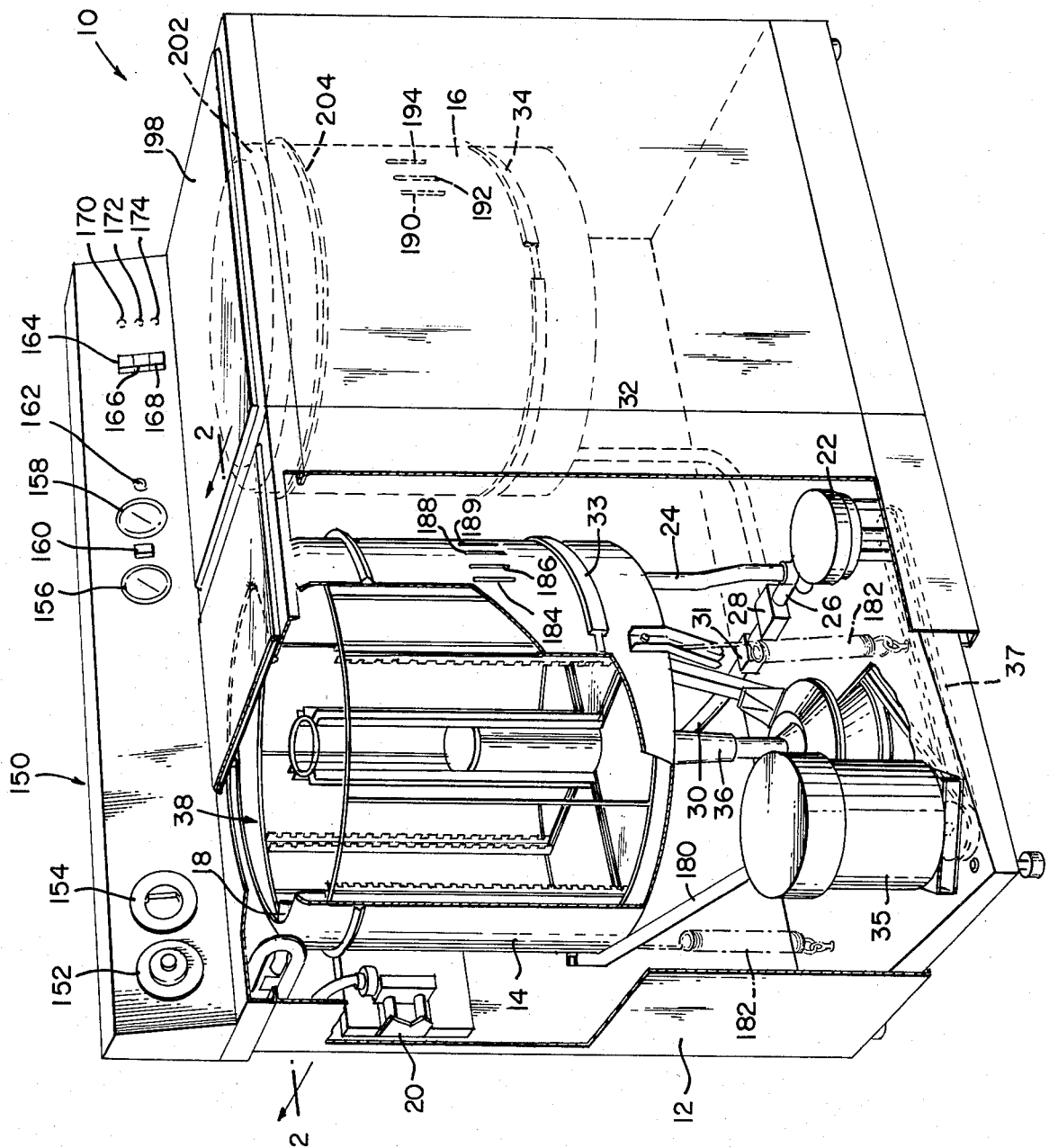
FIG. 1 is an isometric view of the apparatus of the present invention, with portions of the housing broken away to show the operating components.

As indicated previously herein, the present invention is concerned with the thorough and reliable cleaning of hospital equipment used in anesthesia and inhalation therapy. The hollow components, particularly elongate tubing (some of which is corregated), are particularly difficult to clean.

In the present invention, a variety of novel features are incorporated to optimize the overall cleaning operation. First, the basket in which the articles are carried is particularly arranged to optimize the effectiveness of the various steps in the cleaning process (including the initial fill with liquid, the washing action, the emptying step, and the liquid removal or "shake-dry" period subsequent to the emptying). Second, the sequence of initiating the various action is also arranged to optimize performance. Third, the components of the apparatus of the present invention are selected and arranged to accomplish the various actions in an effective manner. Fourth, the control apparatus is arranged to properly carry out the functions of the present invention in correct coordination and sequence.

In the following description, first the main components of the present invention will be described generally. Then each of the four main aspects of the present invention (as noted above) will be described in order.

Main Components of the Apparatus

The apparatus 10 of the present invention comprises a housing structure 12 which contains a cylindrical cleaning tub 14 and a transfer tub 16. A water inlet nozzle 18 sprays water into the upper side of the tub 14, and this water is controlled through a solenoid operated water inlet valve 20.

A pump 22 is positioned below the tub 14 and is connected to the lower side of the tub 14 through a main hose 24. The pump 22 leads through a second section of hose 26 to a diverter valve 28 which in turn connects to a discharge hose 30 (which has a check valve 31 therein to prevent backflow from the line 30) and a transfer hose 32. The discharge hose 30 leads from the valve 28 to some discharge location, and the transfer hose 32 leads from the diverter valve 28 to the lower side of the transfer tub 16.

Each of the tubs, 14 and 16, is provided with a related heating element 33 and 34, respectively. Each heating element 33 and 34 is conveniently provided in the form of a heavy metal band or strap extending circumferentially around its related tub 14 or 16. There is a motor 35 having a first drive transmission 36 and a second belt drive 37 connected to the pump 22.

Containing Basket

The articles which are to be cleaned are placed in a containing basket 38, positioned in the cleaning tub 14. As indicated previously, the arrangement and operation of this cleaning basket 38 are considered to be particularly significant in the present invention to enable the cycles of the present invention to be carried out more effectively. Thus, the construction of this basket 38 will be described prior to describing the cycles of the present invention.

Figures 7, 8:
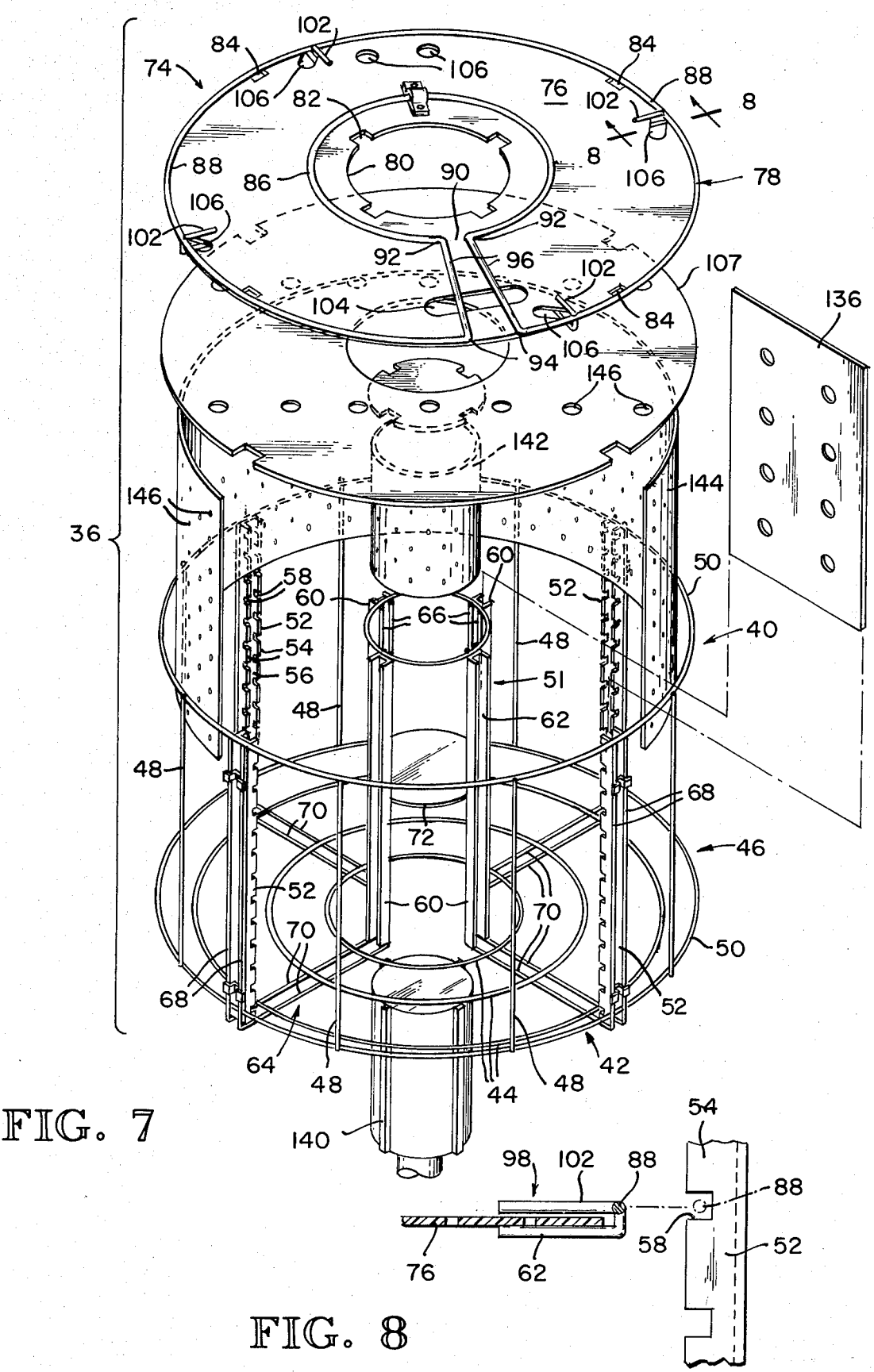
FIG. 7 is an exploded isometric view illustrating the containing basket of the present invention.
FIG. 8 is a view drawn to an enlarged scale, taken along line 8—8 and showing the manner in which a partition member of the basket of FIG. 7 is mounted to the supporting framework.

With reference to FIG. 7, the basket 38 comprises a cage-like cylindrical wire frame 40. It has a bottom portion 42 made up of concentric circular wire members 44, a side portion 46 comprising upright wire members 48 joined at the top and bottom by circular wire members 50, and a hub portion 51.

Positioned at 90° intervals at circumferentially spaced locations on the side portion 46 of the frame 40, there are four vertically aligned posts 52. Each post 52 has two inwardly facing web portions 54 which define therebetween a vertically aligned inwardly facing channel 56. Also, the web portions 54 have a plurality of horizontally aligned slots 58 at regular vertically spaced intervals.

There are also four internal posts 60, with each post 60 being at the same radial location as a related outside post 52. Each internal post 60 defines a radially outwardly facing channel 62 in opposed alignment with the channel 56 and its related post 52.

To mount the posts 52 and 60 to the frame 40, each pair of posts 52 and 60 is provided with a pair of U-shaped mounting wires 64. The internal legs 66 of the wires 64 connect to the inside surface of the internal posts 60, the external legs 68 of the wire members 64 connect to the outside of the related posts 52, and the base portions 70 of the mounting wire 64 interconnect the circular members 44 of the cage bottom 42. One or more interior circular wire members 72 interconnect the internal legs 66 and the internal posts 60 to one another.

The basket 38 has a horizontally aligned partition member 74 adapted to be placed at various selected locations in the frame 40. This partition 74 comprises a circular plate member 76 and a mounting frame 78. The plate member 76 has a center opening 80 to accommodate the hub portion 51 of the frame 40. Further, there are four interior slots 82 at the location of the opening 80 to accommodate the four internal posts 60. In like manner, there are in the plate member 76 four peripheral slots 84 to accommodate the four external posts 52.

The frame 78 has an inner hoop portion 86 positioned below the plate 76 and surrounding the center plate opening 80, and an outer hoop portion 88 at the periphery of the plate member 76. The two hoop portions 86 and 88 each make nearly a full circle, but in the relaxed position of the frame 78 are spaced a short distance from one another so as to leave an arcuate gap 90. The ends 92 of the inner hoop portion 86 are joined to the outer ends 94 of the outer hoop portion 88 by a pair of radially extending arms 96. The outer hoop portion 88 has a plurality of inwardly facing U-shaped mounting brackets 98, having upper and lower arms 102 which fit loosely above and below, respectively, the peripheral portion of the plate 84. These brackets 98 are located at regularly spaced locations around the periphery of the plate member 76.

The plate member 76 is formed with a slot 104, transverse to a radius of the plate 76, this slot 104 extending between and moderately beyond the two radial arms of the frame 78. The frame 78 can be sprung inwardly by a person placing a thumb and finger at opposite ends of the slot 104 and moving the two arms 96 toward one another. This causes the outer hoop portion 88 to contract radially so as to be positioned inside the peripheral slots 84 in the plate member 76. At the location of each U-shaped bracket 98, there are additional slots 106 to permit movement of the related brackets 98 inwardly and laterally relative to the plate member 76.

To mount the partition 74 within the basket frame 40, the partition 76 is first placed above the basket frame 40 with the partition slots 82 and 84 in alignment with, respectively, the posts 60 and 52. Then, the two partition frame arms 96 are moved together to contract the outer hoop portion 88, after which the partition 76 is moved downwardly inside the basket frame 40. When the partition is at the proper vertical location, the two arms 96 are released, so that the outer hoop portion 88 springs outwardly to engage a set of horizontally aligned slots 58 in the peripheral posts 52.

Figure 10:
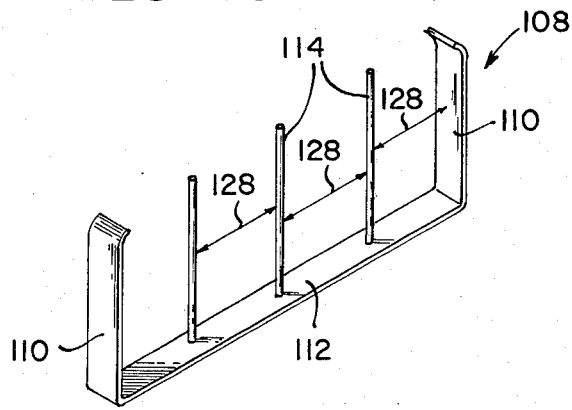
FIG. 10 is an isometric view of one of the spacing components used in the basket shown in FIGS. 7 and 9.

However, prior to placing the partition 74 in the basket frame 40, a bottom plate 107 is placed on the bottom frame portion 42, and the lower portion of the frame 40 is provided with locating and retaining components and then loaded with certain articles which are to be cleaned. With reference to FIG. 10, there is shown a locating member 108, having a generally U-shaped configuration, with two upstanding end legs 110, joined at the lower end by a base 112. A plurality of spacing rods 114 extend upwardly from the base 112 at regularly spaced intervals therealong. The locating member 108 is sized so that the two legs 110 fit in a pair of opposed channels 56 and 62 of a related pair of internal and external posts 52 and 60.

Figure 11:
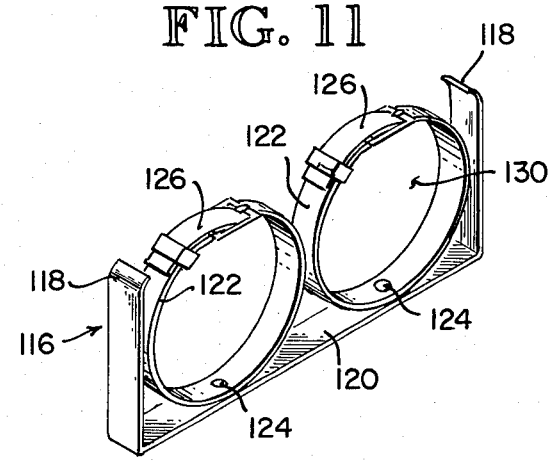
FIG. 11 is an isometric view of one of the retaining members used in the basket shown in FIGS. 7 and 9.

With reference to FIG. 11, there is shown a retaining member 116, also having a U-shaped configuration, and being made up of two upstanding legs 118 joined at the lower ends by a base member 120. Connected to the base member 120 are a pair of chokers or retaining straps 122. Each retaining strap 122 is connected by a center portion at 124 to the base member 120, and the two free ends are provided with a suitable buckle 126 or other fastening means so that the strap 122 can be adjusted to greater or lesser lengths.

To load the basket 38, at least one retaining member 116 is inserted in one set of posts 52–60 so as to be radially aligned in the frame 40. One or more locating members 108 are inserted in other sets of posts 52–60. With the locating member or members 108 being radially aligned, the locating spaces or areas 128 between adjacent spacing rods 114 and legs 116 are circumferentially aligned in the basket frame 40. Likewise, with the one or more retaining members 116 being radially aligned, the retaining straps 122 define retaining cavities 130 that are circumferentially aligned.

With the locating and retaining members 108 and 116 in place, the basket 38 is now ready to receive the elongate tubular articles which are to be cleaned. This is accomplished by placing these tubular articles 132 in the bottom of the frame 40 so that the spacing rods 114 and retaining straps 122 maintain these tubular members 132 substantially parallel to the circumference of the basket 38 (i.e. a substantially uniform distance from the vertical center axis of the basket 38). The buckles 126 of the straps 122 are then fastened in a manner so that the straps 122 retain the tubular members 132 securely in place.

Then, the partition 74 is moved downwardly into the basket frame 40 in the manner described previously herein, and fastened in place immediately above the locating and retaining members 108 and 116. In the particular arrangement of FIG. 9, there is a second level in the lower portion of the basket at which additional tubular members 132 are positioned. This is simply accomplished by placing additional locating member or members 108 and retaining member 116 above the partition 74, and loading this area with additional tubular members 132. Then a second partition can be placed above the second set of locating and retaining members 108 and 116.

Figure 9:
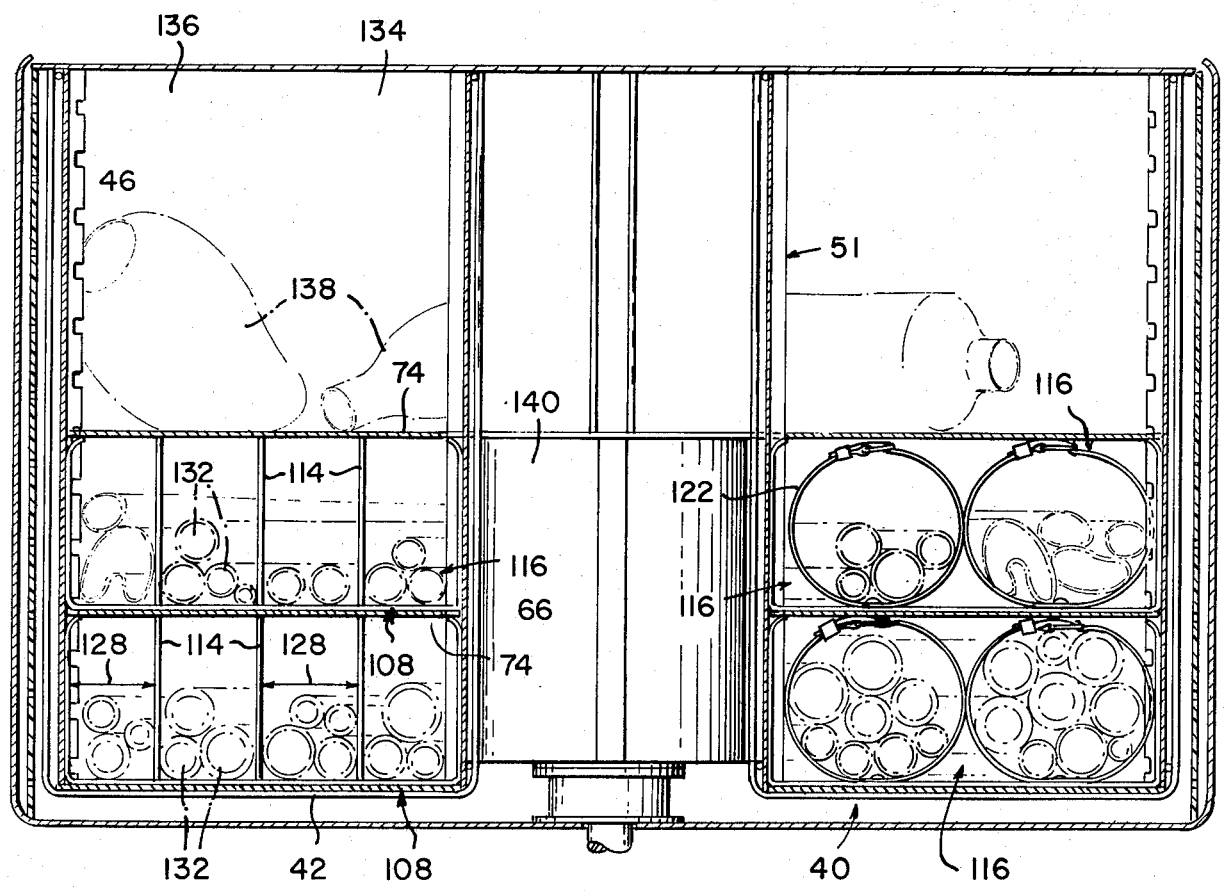
FIG. 9 is a sectional view taken through the vertical center axis of the basket of FIG. 7, illustrating the basket fully loaded for use.

As illustrated in FIG. 9, other articles to be cleaned can be placed in the area 134 above the upper partition 74. This upper area 134 is divided by four vertical partitions or walls 136 which fit in the upper channel portions of the posts 52 and 60. These walls 136 are perforate so as to permit the free flow of water or other liquid therethrough.

In FIG. 9, the basket 38 is shown loaded and ready for operation. It will be noted that the tubular members 132 are securely held in the lower portion of the basket 38 in circumferential alignment. Other articles, such as containers, breathing bags, miscellaneous fittings, etc. (these being generally designated 138) are positioned in the upper area 134 of the basket 38 and are maintained in a quadrant of this upper area by means of the four upper vertical partitions 136. The significance of this particular arrangement will become apparent when the cycles of the present invention are described hereinafter.

At the lower hub portion 51 of the basket 38, there is a hub drive member 140. The interior of this hub member 140 is splined, and the exterior of the hub member 140 is rigidly attached (e.g. by screws) to the four interior posts 60. It is through this hub member 140 that the reciprocating angular motion is imparted to the basket 38.

A small cylindrically-shaped auxiliary container 142 is positioned inside the upper part of the hub portion 51 of the basket 38. This container 142 can be used to retain smaller, possibly more delicate articles, which should not be exposed to the more rapid acceleration experienced by articles in the peripheral portions of the basket 38. Also, a suitable cover 144 is provided around the bottom and side portions 42 and 46 of the frame 40. For ease of illustration, only a portion of this cover is illustrated in FIG. 7. The cover is provided with suitable holes to permit the passage of liquid to the interior and exterior of the cover. Specifically, there are holes 146 at the upper side portion of the cover and at the lower side portion of the cover 144. During a pasteurizing cycle where the pasteurizing liquid is being heated, these upper and lower holes 146 would provide for convection currents of the water positioned between the wall of the tub 14 and the cover 144 and the water within the basket 38.

Operating Cycles

The present invention can be utilized in three cleaning cycles, namely: (a) an initial washing and rinsing cycle, (b) a second disinfect/pasteurize cycle, (c) a third rinse cycle used when a disinfect liquid is used in the second cycle. At this time, the operating knobs and indicators of the apparatus will be described briefly, after which the cycles will be described in order.

With reference to FIG. 1, there is a control console 150 at the upper rear edge of the housing 12. First, there is a cycle selector switch 152. This switch 152 is turned to a location to select the desired cycle, and is pulled out to close the circuitry to initiate the cycle.

Next, there is the pasteurize/disinfect selector dial 154. This dial 154 is used to select the length of time during which the pasteurizing or disinfecting is to take place. There are two temperature indicators 156 and 158. The indicator 156 displays the temperature of the liquid in the cleaning tub 14, while the indicator 158 discloses the temperature of the liquid in the transfer tub 16. Between the indicators 156 and 158 is a heating control switch 160 which is pushed in to cause the pasteurizing liquid or the disinfect liquid to be maintained at a predetermined temperature.

There is a liquid level indicator 162 to indicate the level of liquid in the transfer tub 16. When the liquid in the transfer tub 16 drops below a predetermined level, this indicator 162 lights up.

There are three cycle sequencing switches, 164, 166 and 168. When the first switch 164 is closed, by simply pushing in the member 164, the apparatus will go through only its first wash and rinse cycle. With the switch 166 pushed in, the apparatus will go through not only the first wash and rinse cycle, but also through the second cycle, which can be either a pasteurizing process, or the first portion of a disinfect process. The switch 168 is pushed in to carry the apparatus through the initial wash and rinse cycle and through the disinfect operation of the second cycle, and through the final rinse cycle.

To the right of the switches 164, 166 and 168, there are three indicating lights, 170, 172 and 174. The energizing of light 170 indicates the end of the first wash and rinse cycle initiated by switch 164. The light 172 indicates the completion of the final cycle initiated by switch 166. Finally, the indicator 174 is energized to indicate the completion of the final cycle initiated by the switch 168.

Now the various cycles of the apparatus of the present invention will be described in order.

A. First Cycle (Wash and Rinse)

Initially, the basket 38 is loaded with articles to be washed, as indicated in FIG. 9, and soap or other cleaning medium is thrown into the basket 38. Then the first cycle switch 164 is closed, and the selector switch 152 is moved to the start position and then pulled out to supply current to the apparatus.

Initially, two things happen. The water inlet valve 20 is opened to start water flowing into the cleaning tub 14. Also, power is transmitted to the motor 35 to cause it to operate through the transmission 36 to impart an angular oscillating motion to the basket 38, so that throughout the entire period during which the tub 14 is initially being filled, the basket 38 is oscillating. Thus, part way through the filling period there is sufficient water in the tub 14 to cause a washing action of the tubular members 132 positioned in the lower part of the basket 38.

After the tub 14 has become filled to the desired level so that all of the articles 132 and 138 in the basket 38 are totally immersed, the basket 38 continues to agitate for a suitable washing period, generally about five or six minutes, to provide a washing action. At the completion of this washing period, the motor 35 is stopped, the contacts to the motor 35 are switched so that the motor runs in a reverse direction, and power is again transmitted to the motor 35 to cause it to run in the opposite direction.

Prior to reversing the motor 35, the motor 35 had been driving the pump 22 through the belt 37 in a direction to pump into the tub 14. However, there was no pumping action, since the diverter valve 28 had closed off any communication from the transfer tub 16, and the check valve 31 in the discharge hose 30 prevented any fluid from the hose 30 traveling into the pump 22. With the motor now operating in a reverse direction, two things occur. The motor 35 continues to oscillate the basket 38 in the same manner that it did during the filling and washing periods. Additionally, the pump 22 is operating in a direction to draw out the wash water from the tub 14 and discharge it through the hose 30. (The flow pattern for this first cycle is illustrated in FIG. 4.) When the tub 14 is totally empty, the motor 35 continues to operate to oscillate the basket 38 during a "shake-dry" period, which lasts for about one half to two minutes.

It has been found that with the articles to be washed positioned as indicated in FIG. 9, this oscillating motion of the basket 38 during the "shake-dry" period is particularly effective in removing the remaining droplets of water from the articles, particularly from the tubular members 132 in the lower part of the basket 38. The transmission 36 is so arranged that the angle of oscillation is approximately 180°, and the period of one back-and-forth oscillating motion takes approximately 1½ seconds. It has been found that the droplets in the tubular members 132 tend to migrate to the open ends thereof and fall into the tub 14. Further, the locating and retaining members 108 and 116 maintain the circumferential alignment of the tubular members 132 so that the tendency of the centrifugal force in the oscillating motion to entrap liquid inside the tubular members 132 is greatly alleviated.

Subsequent to the "shake-dry" period, the motor 35 is stopped, reversed and again activated, and the water inlet valve 20 is opened to initiate a rinsing step by directing water into the tub 14 through the nozzle 18. Thus, as rinse water is filling the tub 14, the basket 38 continues to oscillate. When the tub 14 is partially full, the lower positioned tubular members 132 are immersed in the rinse water, so that there is rinsing action during this fill period. When the tub 14 is filled to the desired level to completely immerse all the articles being washed and rinsed, the water inlet valve 20 is closed and the basket 38 continues to oscillate for a predetermined period of time, approximately one to two minutes, to cause a rinsing action.

Then, the motor 35 is stopped, the leads to the motor 35 reversed to cause it to operate in the opposite direction, and the motor 35 is again energized to cause the pump 22 to operate in its discharge mode and draw the rinse water from the tub 14. As the tub 14 is being emptied of rinse water, the basket 38 continues to oscillate. When the tub 14 has been completely emptied, the motor continues to operate for a period of time to continue the oscillation of the basket 38 for a second "shake-dry" period to remove droplets of rinse water from the articles being cleaned.

After the first rinsing process, there is a second substantially identical rinsing process to insure that the rinsing is adequate. With the second rinsing period complete, the light 170 goes on to indicate that the first wash/rinse cycle has been completed. If only switch 164 has been pushed in, the apparatus 10 then stops operating, with the light 170 remaining on. This light 170 will remain on until the cycle selector switch 12 is either pushed in to shut off power or moved to some other position.

B. Second Cycle (Pasteurize/Disinfect)

Normally in using this second cycle, the articles in the basket 38 will be passed through the first wash and rinse cycle prior to either pasteurizing or disinfecting. This would be accomplished by moving the selector switch 152 to the original start position and pressing in the switch 166. If for some reason it is desired to employ only the second cycle, the switch 166 is pushed in, and the selector switch 152 moved to the appropriate location to start the second cycle. In either case, the steps of the second cycle are carried out in the same manner.

Let it be assumed that the switch 166 has been pushed in, and that the apparatus has completed the above described first wash/rinse cycle. Subsequent to the second rinsing, three things happen in sequence in a relatively short period of time. First, the leads to the motor 35 are reversed to cause the motor to operate in a position to cause the pump 22 to pump into the tub 14. Second, the diverter valve 28 is activated to cause the pump 22 to communicate with the transfer tub 16 through the transfer hose 32. Third, the motor 35 is again activated to cause the basket 38 to oscillate and also to cause the liquid in the transfer tub 16 to be pumped into the cleaning tub 14. If a pasteurizing process is selected, the liquid in the tub 16 would be hot water (e.g. 170° F.). If the disinfect process is selected, the liquid in the tub 16 would be a disinfect liquid, either at room temperature or heated to a desired level. If the liquid in the tub 16 is to be at an elevated temperature, then the heating control switch 160 would have been turned "on" previously to insure the liquid is heated to the desired temperature. This would cause the heating element 33 to be energized to bring the liquid in the tub 16 to the desired temperature.

For purposes of description of this second cycle, let it be assumed that it is desired to pasteurize the articles in the basket 38 so that hot water is being transferred from the tub 16. As the tub 14 is being filled by the pump 22 pumping pasteurizing water from the tub 16 into the tub 14, the motor 35 continues to cause the basket 38 to oscillate. When the pasteurizing water in the tub 14 has reached a predetermined level, the diverter valve 28 is closed, after about four minutes the motor 35 is stopped, and a pasteurize/disinfect timer, which was previously set for a predetermined pasteurizing time by means of the selector dial 154, begins to operate. However, the circuitry which activates the pasteurize/disinfect timer is connected in series with a thermostat which senses the temperature in the tub 14. At the time of activating the pasteurize/disinfect timer, control circuitry shuts off power to the heating band 33 for the tub 16 and transfers power to the heating band 34 for the tub 14. If the pasteurizing water has dropped in temperature below a certain level in moving into the tank 14, then the thermostat switch in series with the pasteurize/disinfect current to the pasteurize/disinfect timer until the pasteurizing water in the tub 14 has been brought up to the proper predetermined temperature level. At that time, the pasteurize/disinfect timer will begin traveling through its preselected time period.

During the time period that the pasteurizing (or disinfecting) process is taking place, the motor 35 is inactive so that the basket 38 is not being oscillated. However, as a modification, it would be possible to attach an actuating cam to the pasteurize/disinfect timer to cause the motor 35 to operate for short periods to cause short periods of oscillation of the basket 38, and thus insure that the liquid in the tank 14 is in proper contact with the articles which are being pasteurized or disinfected.

At the completion of the pasteurizing or disinfecting period (i.e. when the pasteurize/disinfect timer, as set by the dial 154, has completed its operation), the leads to the motor 35 are reversed to cause it to operate in a reverse direction, the diverter valve 28 is activated to cause the pump 22 to communicate with the transfer tub 16, and the motor 35 is then activated to cause the liquid in the tube 14 to be moved back to the transfer tub 16. The pattern of flow for this second cycle from the tub 16 to the tub 14 and back into the tub 16 is shown schematically in FIG. 5. While the tub 14 is being emptied, the motor 35 continues to oscillate the basket 38.

At the completion of the emptying period, the motor 35 continues to operate to oscillate the basket 38 through another "shake-dry" period and remove the liquid (either pasteurize liquid or disinfect liquid) from the articles in the basket 38. At the completion of this "shake-dry" period the motor stops, and the light 172 is turned on to indicate that the second cycle has stopped. If the third switch 168 has not been pushed in, the apparatus ceases to operate, and the light 172 remains on until the selector switch 152 is moved or pushed in.

If a pasteurizing process is being carried out, there is no need for any subsequent rinse, so the overall pasteurizing process is complete. However, if the disinfect method is being used, it is generally necessary to rinse the disinfect liquid from the articles in the tub 38. Thus in employing the disinfect process, the switch 168 would also have been closed or the switch 168 can simply be closed at the completion of the second cycle.)

C. Third Cycle (Final Rinse)

As indicated above, this final rinsing cycle is normally used only at the completion of the previous cycle where a disinfecting liquid is used. Thus, under normal circumstances, the switch 168 would be closed, and the apparatus 10 would have already gone through the first wash/rinse cycle, and a second cycle using the disinfecting liquid from the tub 16. With the switch 168 closed, the apparatus 10 automatically goes into this third final rinsing cycle after the second cycle has been completed.

At the beginning of this third cycle, the leads to the motor 35 remain in the position to cause the motor 35 to run in reverse and thus drive the pump 22 in a direction to discharge liquid from the tub 14. Then, the water inlet valve 20 is open to cause to spray of rinse water to be discharged through the nozzle 18 onto the articles in the basket 38. Very shortly thereafter, the motor 35 is activated for a short period of time (e.g. 30-45 seconds) to cause the pump 22 to draw out and discharge to the sewer the water being sprayed into the tub 14. Then, the motor 35 is stopped, the leads to the motor 35 reversed, and the motor again activated to oscillate the basket 38, without draining any water from the tub 14, since the pump 22 is operating in its "pump in" direction with the diverter valve 28 closed to the tub 16. The water inlet valve 20 remains open and rinse water continues to flow into the tub 14 to fill the tub for the first rinse in this third cycle.

From this point on in the cycle, the apparatus operates in substantially the same manner as it did in the two rinsing steps carried on in the first cycle. Therefore, these will be summarized only briefly at this point of the description. At the completion of the filling of the tub 14 with rinse water, the basket 38 is oscillated for a short period of time (e.g. one to two minutes to provide a rinsing action), after which the rinse water is discharged from the tub 14 while the basket 38 continues to oscillate. As described previously herein, when the rinse water has been completely discharged from the tub 14, the basket 38 continues to oscillate for about two minutes through a "shake-dry" period. Thereafter, a second rinsing process is carried out in the same manner. The flow pattern for this third cycle is shown in FIG. 6, and it will be noted that this is the same flow pattern as for the final cycle, as shown in FIG. 4. At the completion of the second rinse, the third indicator light 174 goes on to indicate the completion of the final cycle. This light 174 remains on until the selector switch 152 is either moved to another location or opened.

Further Description of the Apparatus

Earlier in this description under the heading "Main Components of the Apparatus", there is a description only of those components necessary for a basic understanding of the operating cycles of the present invention. There will now be described the remaining components of the present invention.

It has been found that the apparatus of the present invention can be manufactured quite economically by making modifications to a conventional washing machine used for washing clothes. The particular washing machine which was adapted for the present invention is one sold in the United States under the trademark "MAYTAG", having a "sud-saving" feature. The "sudsaver" feature enables the wash water to be transferred to some storage location, and then be pumped back into the wash tub for a subsequent washing. In the following description, the components of the present invention which were part of the original Maytag washing machine will be identified, and the manner in which some of these components were modified will be described.

The housing 12 of the apparatus 10 is simply made up of two cabinets of two separate washing machines placed side by side. The control console 150 and the control circuitry and components therein (to be described hereinafter) are quite different from the conventional clothes washing machine, so these are added as new components. The cleaning tub 14 is the same cleaning tub in the original Maytag washer. However, the impeller of the Maytag washer is removed, and is replaced by the basket 38 of the present invention. This tub 14 is supported by three legs 180. Also shown for purposes of illustration are three springs 182 (shown in broken lines) which are part of the original equipment of the Maytag washing machine. However, since in the present invention no "fast spin rinse" action is used, these springs 182 can be removed if desired.

With regard to the transfer tub 16, it has been found that this can be provided quite economically simply by taking a conventional washing machine, and removing all the components except the cabinet and the tub 16. If desired, legs 180 can be provided, or the tub 16 can be suspended from an upper edge portion of the housing 10 surrounding the tub 16.

The spray nozzle 18 and solenoid valve 20 are existing equipment in the Maytag washing machine. However, the cold water inlet is permanently closed so that only hot water is directed by the solenoid valve 20 to the nozzle 18.

The pump 22, hose 24, hose 26, diverter valve 28, discharge hose 30 and transfer hose 32 are or may be the components previously existing in the Maytag washing machine. However, the check valve 31 (not conventional equipment in the Maytage machine) is added as a new component. This check valve 31 has two functions. First, it prevents any back flow from the discharge line 30. Secondly, the check valve 31 has a second check valve element which permits an inflow of air into the check valve 31 and to the pump 22, while preventing an outflow of air. This permits the pump 22 to function properly in the "pump in" direction when the diverter valve 28 is closed to the transfer hose 32.

The heating bands 33 and 34 are not components of the Maytag washer, and are provided to perform particular functions peculiar to the present invention. Also, there are four temperature sensing elements placed on the sidewall of the tub 14, these being designated 184, 186, 188 and 189. Further, there are three other temperature sensing elements mounted on the sidewall of the tub 16, these being designated 190, 192 and 194, respectively. The particular functions of these sensing elements 184–194 will be described in more detail in the later description of the circuitry of the present invention.

With regard to the construction of the top portion of the housing 12, there are two lids, 196 and 198, respectively, with the lid 196 closing the tub 14, and the lid 198 closing the tub 16. Fixedly connected to each of the lids 196 and 198 are a related one of two covers, 200 and 202, each joining to its related tub 14 or 16 at a juncture line 204. It is possible to incorporate the covers 200 and 202 as part of the lids 196 and 198 for the reason that there's no substantial oscillation or vibration of either of the tubs 14 and 16 during any of the three cycles of the present invention.

The motor 35 is the existing motor in the Maytag washing machine. However, the circuitry for the motor 35 is arranged so that the motor 35 operates at only one speed, whether it is operating in its forward or reverse direction. The belt drive 37 to the motor 22 exists in the Maytag washing machine.

The main transmission 36 of the present invention is a modification of an existing transmission of the above mentioned Maytag washing machine. The manner in which this transmission is modified to provide the transmission 36 is believed to be a novel feature of the present invention, and thus will be described in detail herein. First, the main components that existed in the previous Maytag transmission will be described, and then the manner in which these are modified to accomplish the functions of the present invention.

Figure 2:
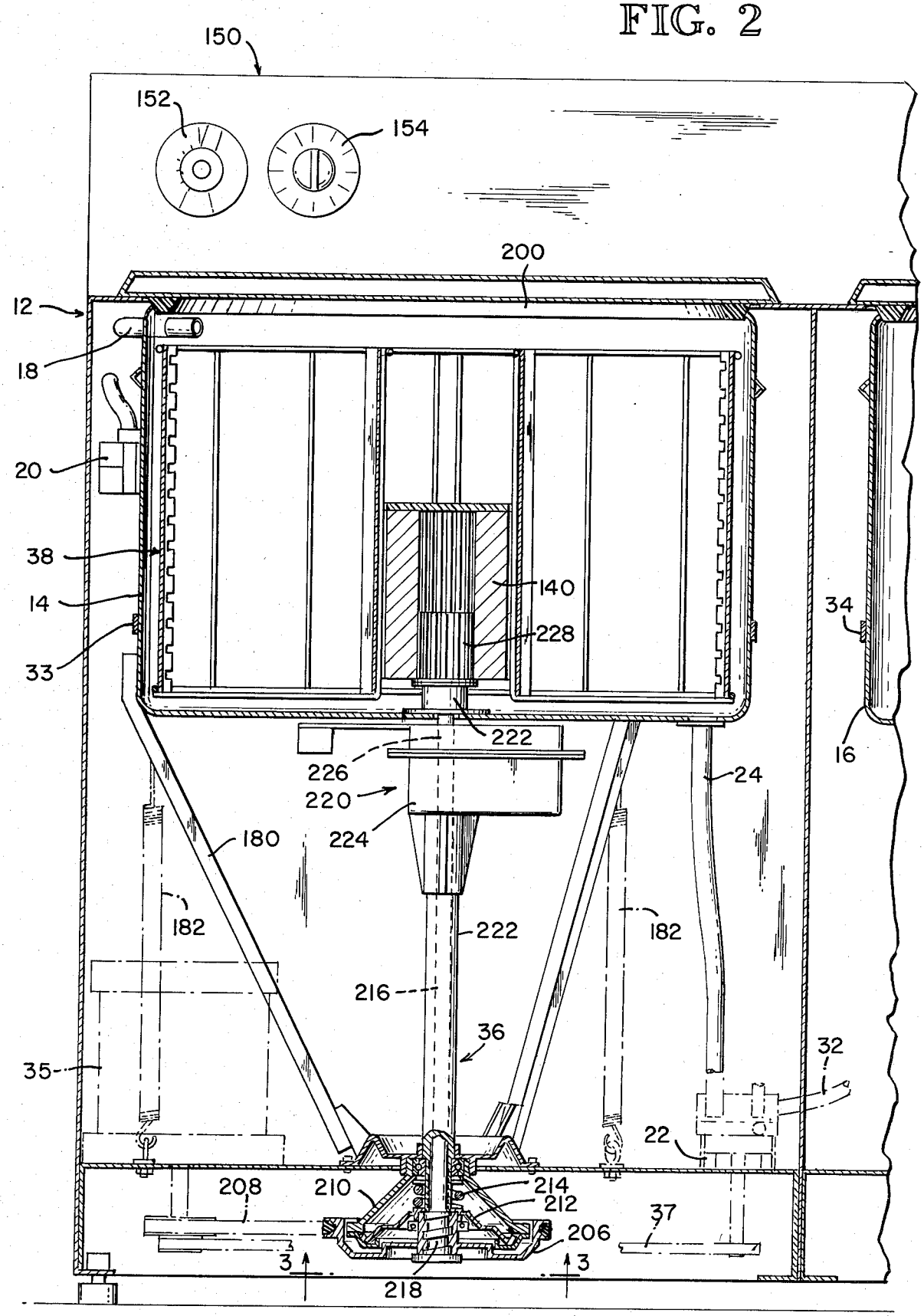
FIG. 2 is a front elevational view of the cleaning portion of the apparatus, with the front portion of the housing removed.

With reference to FIG. 2, there is at the lower end of the transmission 36 a main drive pulley 206, driven from the motor 206 by means of a belt 208. There is a brake housing 210 having a lower circular portion positioned within the periphery of the drive pulley 208, and extending upwardly and inwardly in a frusto-conical configuration to join to fixed structure. Inside the brake housing 210 is a brake drum 212 which is pressed downwardly by a helical spring 214 to engage the brake housing 210 and thus be in a braking position.

There is an inner drive shaft 216 having at its lower end helical threads 218 which engage matching helical grooves in the center of the drive pulley 206. This shaft 216 extends upwardly to a gear transmission 220. Surrounding the drive shaft 216 is an elongate sleeve 222 having at its lower end a spline connection to the brake drum 212. The upper end of the sleeve 222 is fixedly secured to the housing 224 of the gear transmission 220.

When the motor 35 is run in a forward direction, the shaft 216 is caused to rotate in a clockwise direction (as seen from the top in FIG. 2). With the shaft rotating clockwise, the brake drum 212 remains in braking engagement with the housing 210 so that the brake drum 212 holds the sleeve 222 stationary, by virtue of the spline connection between the drum 212 and the sleeve 222. The shaft 216 then transmits power through the gear transmission 220, this transmission 220 translating the rotary motion of the shaft into a rotary oscillating motion which is imparted to an upper shaft member 226. This shaft member 226 has at its upper end a spline connection 228 with the hub 140 of the basket 38. Thus, a rotational oscillating motion is imparted to the basket 38.

The components described thus far relative to the power transmission 36 all are present in the above mentioned existing Maytag washing machine. Further, the mode of operation described immediately above, where the shaft 216 operates through the gear transmission 220 to translate rotary motion into oscillating motion, is also the normal mode of operation of the transmission existing in the above mentioned Maytag washing machine. With regard to the gear transmission 220, this is or may be of conventional design, and one such transmission is shown in FIG. 3A.

The power input from the shaft 216 is to a gear 230, which in turn acts through a set of speed reducing gears 232 to drive a gear 234. One end of a drive arm 236 is rotatably connected at 238 to the gear 234 at a location spaced from the center of rotation thereof, and the opposite end of the arm 236 is connected at 240 to a second drive arm 242.

This second drive arm 242 is pivotally connected by one end at 244 at a location spaced from the connection 242 to the gear transmission housing 224. The other end of the second drive arm 242 is provided with a set of gear teeth 246 which engage yet another gear 248 that is fixedly connected to the upper shaft member 226.

It is readily apparent from an examination of the gear and drive arm components 230 through 248 that rotation of the gear 230 causes rotation of the gear 234 at a relatively slower speed to in turn cause the arm 236 to oscillate back and forth. This in turn moves the second drive arm 242 back and forth to cause the gear 248 to oscillate angularly and in turn cause angular or rotational oscillation of the upper shaft member 226.

The above described mode of operation of the components of the transmission 36 is a conventional mode of operation of these same components in the above mentioned Maytag washing machine. This same mode of operation, caused by the motor 35 being operated in a forward direction, occurs in the present invention. That is to say, with the motor 35 rotating in a forward direction, the shaft 216 rotates clockwise and acts through the gear transmission 220 to oscillate the spline member 228 and cause rotational oscillating motion of the basket 38.

However, let it now be assumed that the motor 35 is reversed so that the rotation of the pulley 206 is reversed, with it now rotating in a counter-clockwise direction. In the operation of the afore-mentioned Maytag machine, this causes the pulley 208 to climb the threads 218 of the shaft 216 and force the brake drum 212 out of engagement with the brake housing 210. This also moves the pulley 208 out of locking engagement with the lower end of the shaft 216, so that now the shaft 216 drives directly through an engaged clutch element between the shaft 216 and sleeve 222 to cause the sleeve 222 to rotate with the shaft 216. Since the sleeve 222 is fixedly connected to the gear transmission housing 224, the entire housing is caused to rotate and in turn rotate the upper spline connection 228, which in the afore-mentioned Maytag machine would be attached to an inner container within the tub 14. In the Maytag machine, when the motor 35 rotates in reverse, it is rotating at high speed. Thus, in the reverse mode of operation, the motor 35 would rotate the entire shaft 216, sleeve 222, gear transmission 220, and gear transmission housing 224 as one unit to cause high speed rotary motion of the inner container of the Maytag washing machine.

It is apparent that this high speed rotational motion of the gear transmission 36, as it occurs in the conventional Maytag washing machine, is not desired in the present invention. However, in adapting the Maytag washer to the present invention, it is necessary to operate the motor 35 in both its forward and reverse direction to cause the pump 22 to operate in both its "pump in" and "pump out" modes so that all of the operations in the various cycles can be accomplished. One solution to this would be to provide one reversible motor for the pump 22, and a second uni-directional motor to act through the transmission 36. However, as a feature of the present invention, the transmission 36 was modified in a quite simple manner to adapt this apparatus to operate according to the cycles of the present invention.

Reference is made to FIG. 3, which shows the drive connection between the pulley 208 and the lower end of the inner drive shaft 216. In the conventional Maytag machine, the lower end of the shaft 216 has an outwardly protruding element 250 having an arcuate length of about 30°. The pulley 206 has an inwardly protruding element 252 adapted to engage the element 250 of the shaft 216. This element 252 has an arcuate length no greater than about 60°, so that limited angular relative rotation of about 270° is permitted between the pulley 206 and the shaft 216. This limited relative rotation permits the pulley to positively engage the shaft 216 when the motor 35 is operating in its forward mode. It further permits sufficient relative rotation between the shaft 216 and the pulley 206 to move the brake drum 212 out of engagement with the brake housing 210 to place the apparatus in its high speed spin rotation.

In the present invention, the transmission 36 was modified simply by placing the two elements 250 and 252 against one another in drive relationship, and then placing an arcuate blocking element 254 around the lower end of the shaft 216 so that no relative rotation is permitted between the pulley 206 and the shaft 216. With the blocking element 254 in place, when the motor 35 goes into its reverse mode of operation, the brake drum 212 does not move out of engagement with the housing 210. Accordingly, the gear transmission 220 remains stationary and the shaft 216 simply acts through the gear transmission 220 to cause oscillating motion of the upper shaft member 226 to rotate the basket 38 angularly through the spline connection 228. Thus, in both the forward and reverse mode of operation of the motor 35, the basket 38 oscillates angularly in substantially the same manner.

Control Apparatus

Figure 12:
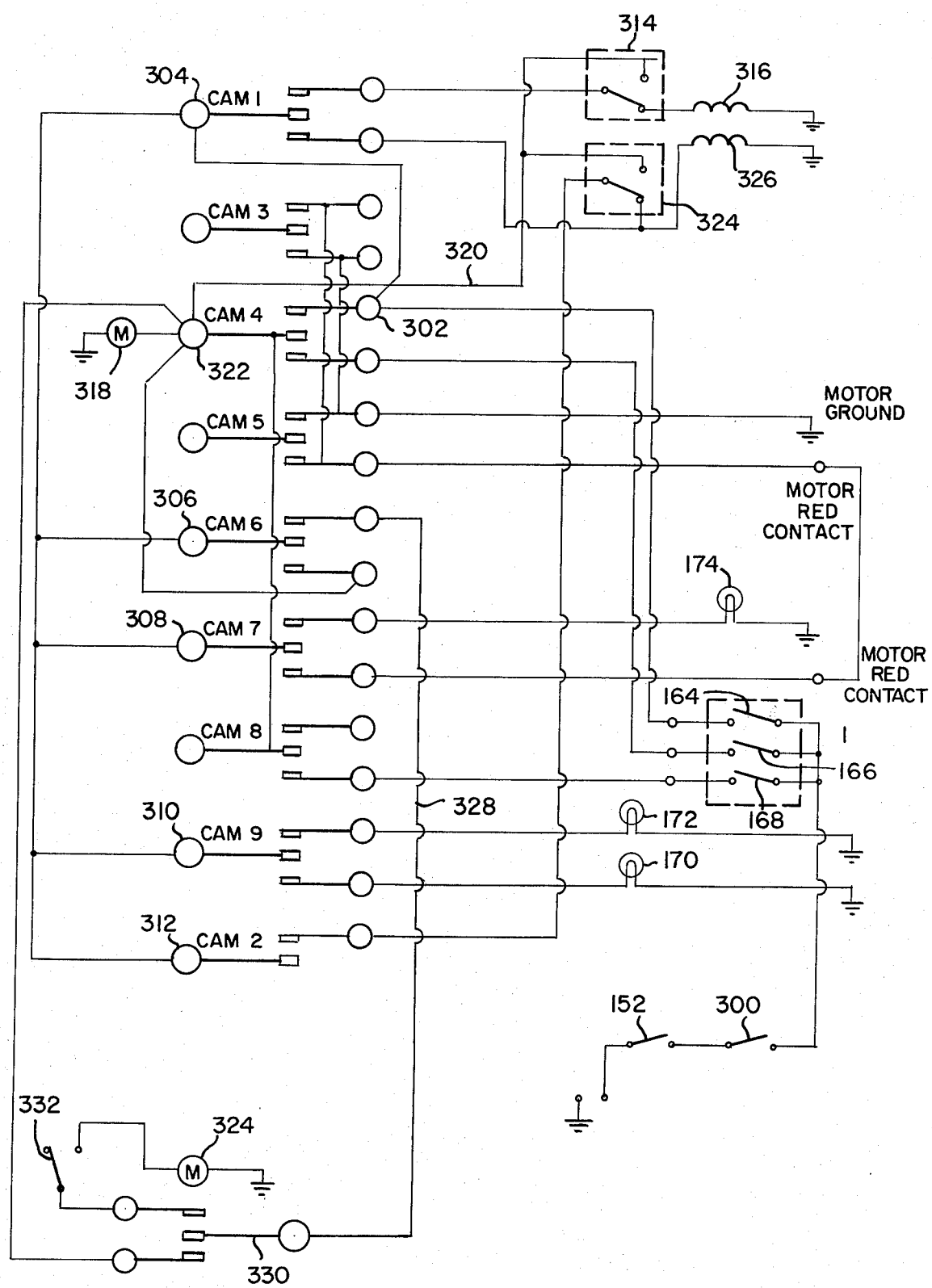
FIG. 12 is a wiring diagram of the control apparatus of the present invention.
Figure 13:
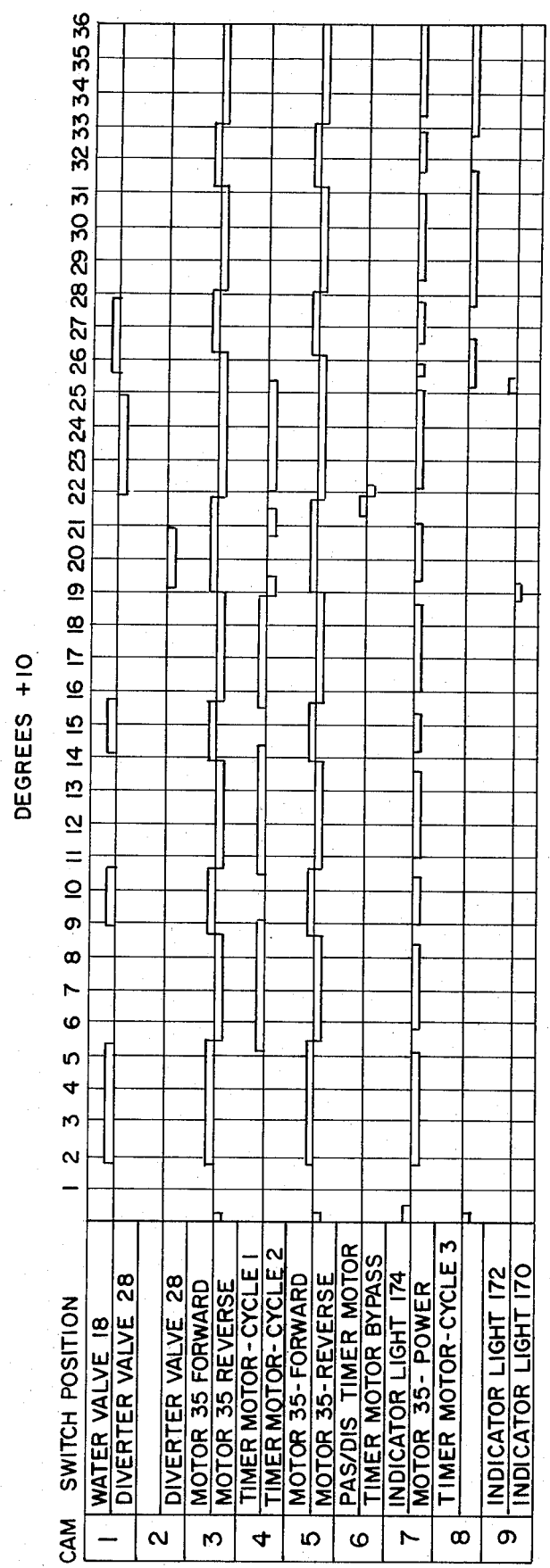
FIG. 13 is a cam diagram illustrating the operation of the control apparatus of the present invention.

The control apparatus of the present invention comprises nine cam members operatively connected to the cycle selector switch 152. Each cam has an associated cam switch, and is capable of moving its switch in either an upper direction to engage an upper contact or a lower direction to engage a lower contact. FIG. 13 is a schematic drawing illustrating the sequence by which the cams move their switch elements to make either upper or lower contact to cause the components of the apparatus to move through all the operating cycles. FIG. 12 illustrates the circuitry through which the cams act.

The description of the control apparatus will be divided into three sections, each relating to a specific one of the operating cycles.

A. First Cycle (Wash and Rinse)

Let it be assumed that the apparatus is to go through the first wash/rinse cycle only. Accordingly, the cycle selector button 164 is pushed in, and the cycle selector 152 is rotated to the "start" position and then pulled out to transmit power through the circuitry. This action will cause the entire first cycle to proceed to completion, after which the indicator light 170 will be turned on to indicate completion of the first cycle.

Reference is made to FIG. 13. To start the cycle, the cycle selector 152 is moved to the 18° point on the timing chart shown in FIG. 13. The area between the 2° and the 18° location is an "off" area, and the cycle selector switch 152 must be moved manually through that area. This is actually accomplished by pushing the cycle selector switch 152 in, and then turning it to the 18° location, after which it is pulled out.

Reference is now made to FIG. 12. When the cycle selector switch 152 is pulled out, it is moved from its open position (shown in FIG. 12 to its closed position. Also, there is a lid switch 300 in series with the switch 152, this switch 300 being closed by the closing of the lid 196 onto the tub 14. Further, with the cycle selector switch 164 closed, voltage is transmitted to certain points in the circuitry to make them "hot", these being designated as follows: point 302, which is the upper contact point of the switch of cam 4; point 304 which is the contact point for the pole of the switch of cam 1; point 306 which is the contact for the pole of the switch of cam 6; point 308, which is the contact for the pole of cam 7; point 310 which is the contact for the pole of the switch of cam 9; and point 312 which is the contact point of the pole of the switch of cam 2. At this stage, voltage is supplied to all of the points which are necessary to enable the apparatus to move through the entire first wash/rinse cycle.

Reference is now made to the timing chart of FIG. 13. The darkened areas indicate where the pole of the switch of a particular cam has moved either upwardly or downwardly, depending on whether the darkened area is on the top or the bottom line of that particular cam, and the light areas indicate where the pole is in a non-contact middle position.

With the switch 152 moved to the 18°+ position and pulled out to make contact, several things occur. First, the switch of cam 1 moves to its up position to cause current to flow through a liquid level switch 314 to a solenoid 316 which opens the water valve 20 and permits hot water to flow into the tub 14. The liquid level switch 314 is in its "down" position, which indicates that liquid in the tub 14 has not reached a predetermined "full" level.

At the same time, the switch elements of cam 3 and cam 5 are caused to be moved to an "up" position. The switch elements for cam 3 and cam 5 serve the sole function of reversing the motor 35. When the switch elements cam 3 and cam 5 are in an "up" position, the motor is caused to operate in its forward mode. When the switch elements of cam 3 and cam 5 are moved to the "down" position, the motor 35 is caused to move in its reverse direction. At the same time as the switches of cam 1, 4 and 5 are moved, the switch element of cam 7 is moved downwardly to transmit power to the motor 35 so that the motor 35 begins to rotate in its forward mode.

With further reference to FIG. 12, there is a timer motor 318 which, when activated, rotates the cams 1-9 at a proper rate of travel. It will be noted that in the situation described above, (with power being transmitted to the solenoid 316 to cause the valve 20 to open to direct water into the tub 14, and with the motor 35 operating to cause oscillating rotational movement of the basket 38), no power is being transmitted to the timer motor 318. Thus, the timing sequence is stationary during the filling of the tub, and if because of variations in water pressure it takes a longer time for the tub 14 to fill, the overall timing of the cycle is not changed.

When the water in the tub reaches a predetermined level, it causes the liquid level switch 314 to move to its up position. This shuts off power to the solenoid 316 so that the valve 20 is closed, and at the same time, it transmits power through line 320 to contact point 322 to provide power to the timer motor 318 and thus cause the cams to begin rotating at a properly timed rate. This terminates the initial fill period of the first cycle, and begins the period of washing, where the basket 38 is oscillated while the tub 14 is full with wash water.

With reference to FIG. 13, by the time the timer motor has moved the cams to the 52° location, cam 7 causes its switch element to move to a middle "no contact" position to interrupt power to the motor 35. Also at the 50° location, the switch for cam 4 makes upper contact to make connection with point 302 and provide a power connection to the timer motor 318. The reason for this is that at the 54° location, the switch of cam 1 is to move to its no contact position, and it is desired to maintain power to the timer motor 318. The essential function of the upper contact of cam 4 is to maintain power to the timer motor 18 during the proper time intervals throughout the first cycle.

When the timer motor 318 has moved the cams to the 55° location, the cams 3 and 5 cause their switching elements to move into bottom contact to change the direction of the motor. At the 58° location, cam 7 again makes lower contact to energize the motor 35, so that the motor begins to run in the "reverse" direction. This causes the pump 22 to operate in its "pump out" mode to pump the wash water from the tub 14 into the discharge line 30. At the same time, the motor 35 acts through the transmission 36 to cause the basket 38 to oscillate angularly during the emptying period.

It will be noted that this mode of operation continues until the timer motor 318 has moved the cams to the 84° location. However, the components are so arranged that prior to the time the cams reach the 84° location, the wash water has been completely drained from the tub 14. Thus, during the first portion of the time period from the 58° point to the 84° point, the tub 14 is emptying, and during the latter portion of that period, the basket 38 continues to oscillate while the tub is still empty, so that the "shake off" operation can be accomplished subsequent to the draining of the wash water.

At the 87° point, the cams 3 and 5 act to switch the direction of the motor 35. At the 89° location, cam 1 moves its switch to the up position to again make contact with the solenoid 316 for the water switch 20, thus causing hot water to again flow into the tub 14 to initiate the rinsing operation. At the 90° point, cam 7 causes its switch to make lower contact to again cause the motor 35 to operate to oscillate the basket 38 while rinse water is pouring into the tub 14. At the 93° point (i.e. about twenty seconds after the water has begun to flow into the tub 14), the switch for cam 4 drops out of contact to stop the timer motor 318 from operating. When the tub 14 has filled, the water level switch 314 is moved to its up position to break contact to the solenoid 316 and stop water from pouring into the tub 14, and also to make contact through line 320 to point 322 and supply power to the timer motor 318 to cause the cams to again begin rotating through the timing cycle.

With the tub 14 filled with rinse water, the motor 35 continues to cause the basket 38 to oscillate until the timer motor 318 has moved the cams to the 104° point, at which time the switch of cam 7 drops out of contact and causes the motor 35 to stop. Also, at the 105° point, cam 4 causes its switch to make upper contact so that the timer motor continues to run after cam 1 has caused its switch to move out of contact at the 107° point. Also at the 107° point, the switches of cams 3 and 5 reverse so that when the motor 35 is again energized by cam 7 moving its switch to the lower contact at the 110° point, the motor will be caused to operate in the reverse direction. This causes the pump 22 to pump out the rinse water, while the motor 35 continues to act through the transmission 36 to angularly oscillate the basket 38.

The tub 14 empties in a short period of time, and as the motor continues to operate until the 136° location, there is in the latter portion of this time period a "shake-dry" period where droplets of water in the equipment being washed are shaken free of the equipment. This completes the first rinsing process.

At the 139° point, a second rinsing process is initiated, substantially similar to the first rinsing process just described. Accordingly, a detailed description of this second rinsing process will not be given herein. However, to describe the termination of this second rinsing process, at the 189° location, it will be noted that the switch of cam 4 drops out of contact. The switch of cam 4 is so arranged that as soon as it drops out of contact with its upper point, it drops down to its lower contact. However, since the second selector switch 166 is not closed, power is interrupted to the timer motor 318, and the cams proceed no further through the timing sequence. Accordingly, the first wash/rinse cycle has been terminated. At the 188° point, cam 9 has caused its switch to make bottom contact to transmit power to the indicator light 170 to signal the end of the first cycle. This light 170 will remain on indefinitely until someone either pushes in the cycle selector switch 152 to break contact or until the cycle selector switch 152 is moved to some other position.

B. Second Cycle (Pasteurize/Disinfect)

As indicated previously, the second pasteurize/disinfect cycle is usually preceded by the first wash/rinse cycle. To cause the apparatus to operate through both cycles, the switch 166 is moved to a closed position, and the switch 152 is moved to its 18° "start" position and pulled out. (The switch 166 is interconnected to the switch 164 in a manner that closing the switch 166 automatically closes the switch 164.) If it is desired to move directly to the second cycle without going through the first cycle, then the switch 152 is simply moved to the 189° location, and the switch 166 is also closed.

For purposes of description, let it be assumed that the apparatus has moved entirely through the first cycle, so that the cams are at the 189° location, and that the switch 166 has been closed in addition to the switch 164. When the switch of cam 4 drops to its "down" position, with switch 166 closed, power continues to be transmitted to the timer motor 318 to cause the cams to continue to rotate.

At the 190° point, cams 3 and 5 cause their switches to make contact so that the motor 35 will operate in its forward mode. At the 191° mark, cam 2 causes its switch to make contact and transmit power through a second level indicator switch 324 positioned in the tub 14. With the tub 14 empty, the switch 324 is in its "down" position to make contact with a solenoid 326, which when activated moves the diverter valve so that the pump 22 communicates through the line 32 to the transfer tub 16.

Next, at the 193° point, cam 7 closes to the lower contact to cause the motor 35 to run in the forward mode and to oscillate the basket 38, and at the same time to power the pump in its "pump in" mode to pump liquid (either a disinfectant liquid or hot water for pasteurizing) from the tub 16 into the tub 14. When the cams reach the 195° point, cam 4 moves its switch arm out of contact so that the timer motor 318 stops. However, the motor 35 continues to run so that the pump 22 continues to pump the liquid from the tub 16 into the tub 14. If there is not sufficient liquid in the tub 16 to fill the tub 14 to an adequate level, the liquid level switch 324 will not close, and the cycle will not continue. However, on the assumption that there is sufficient liquid in the tub 16, at the time the liquid in the tub 14 reaches a predetermined level, the second level switch 324 moves to the up position to make contact with the timer motor through line 320 and cause the cams to again begin moving through the timing sequence. When switch 324 moves to its up position, it closes the diverter valve 28 from tub 16. During the time period that the cams move from the 195° point to the 209° point, the components are arranged so that the motor 35 continues to oscillate the cage 38 for a period of about four minutes after the tub has been filled. The reason that the switch of cam 2 remains closed during the period from 195° to 209° is to maintain contact with the timer motor.

It will be noted that at the 207° point, cam 4 has caused its switch to close with the bottom contact to maintain a current through the timer motor. At the 211° point, the motor 35 becomes deactivated to stop oscillating the basket 38 and also to stop the pump 22. However, the pump 22 is deactivated after the second level switch 22 moved upwardly to deactivate the solenoid 326 to permit the diverter valve 28 to close off communication with the transfer tub 16.

At the 213° point, the cam 6 makes upper contact to cause power to be transmitted through line 328 to switch 330, operatively connected to the pasteurize/disinfect timer 154. In the preferred form of the present invention, the timer 154 can be set to run through a selected period anywhere from zero to seventy-two minutes, depending upon how long the operator wishes the pasteurizing or disinfect liquid to maintain contact with the equipment being cleaned in the tub 14. At the time the operator moves the timer 154 to the desired position, movement of the timer 154 automatically moves switch 330 to its up position so that power is transmitted to a thermostat 332 which is in turn made responsive to the first temperature sensing element 184 on the tub 14. The thermostat 332 is arranged to close when the temperature is at or above a predetermined temperature level. When the thermostat 332 closes, this transmits power to the pasteurize/disinfect motor to cause the timer 154 to begin moving through its pre-set time period. As indicated previously, the setting of the timer 154 will depend upon the amount of time it is desired to keep the equipment in the tub 14 in contact with the disinfect or pasteurizing liquid. During the period that the pasteurize/disinfect timer 154 is operating, the timer motor 318 for the selector switch 152 is inactive.

When the motor 334 has moved the pasteurize/disinfect timer 154 back to its zero position, it makes contact with the switch 332 to move it to its bottom contact position to cause the top contact of the switch of cam 6 to go into electrical contact with point 322 to energize the main timer motor 318. Thus, from the 213° point to the 219° point, the switch 330 moves the main timer to the 219° point.

At the 218° point, the cams 3 and 5 have caused their switch elements to make lower contact so that the motor 35 will then move in its reverse mode for pumping out action. At the 219° point, the cam 6 causes its switching element to drop to its lower position to maintain power to the timer motor 318. The cam 6 maintains lower contact from the 219° point to the 222° point. This enables cam 4 to make lower contact at the 220° point and carry the timer through to the 253° point.

At the 219° point, cam 1 has made bottom contact to energize the solenoid 226 for the diverter valve 28 to cause the pump 22 to again communicate with the transfer tub 16. Then at the 221° point, cam 7 causes its switch element to make lower contact to again energize the motor 35 so that it operates in its reverse mode and starts the pump 22 pumping the pasteurizing or disinfect fluid back to the transfer tank 16. During the period that the timer moves from the 220° point to the 249° point (e.g. about four and a half to five minutes), the pump 22 initially pumps out all of the liquid from the tub 14, and in the latter portion of this time period, with the tub 14 substantially empty, the motor 35 will continue to act through the transmission 36 to agitate the basket 38 back and forth to shake off excess liquid.

At the 249° point, cam 1 causes its switch element to be moved to a middle out of contact position so that the diverter valve 28 closes the transfer line 32 to the pump 22, and shortly thereafter, at the 251° point the motor 35 stops, by reason of the cam 7 moving its switch element out of bottom contact. At the 250° point, cam 9 makes top contact to energize the second indicator light 172 to signal that the second cycle has come to an end. The cam 4 still has bottom contact, and moves the timer forward to the 253° point, at which time the second cycle actually ends.

As indicated earlier herein, it would be possible to energize the motor from time to time during the period that the pasteurize/disinfect timer 154 is running. This could be accomplished through a cam mechanism attached to the timer 154 directing energy to the motor at periodic intervals. The reason that there would not be constant agitation of the basket 38 during the entire pasteurize/disinfect cycle is that this may cause unnecessary wear on the articles being cleaned. According to the present state of the art, it is only necessary to have complete immersion and contact in the pasteurizing or disinfect liquid to accomplish these properly.

C. Third Cycle (Final Rinse)

As indicated previously, this final rinse is generally utilized only after the completion of the second cycle where a disinfect liquid has been used. To initiate the final rinse, it is necessary that the switch 168 be closed. (Closing switch 168 automatically closes the switches 164 and 166.) Let it be assumed that the second cycle has run its course so that the cams are at the 253° point. At this point, cam 8 has already made lower contact (i.e. at the 251° point), so that with switch 168 closed, the timer motor 318 continues to move the cams beyond the 253° point and through to the 267° point.

At the 255° point, cam 1 moves its switch element to its top position to energize the solenoid 316 and cause the hot water to flow through the nozzle 18. The nozzle 18 is arranged so that the water sprays outwardly over the equipment in the basket 38. Very shortly thereafter, at the 256° point, the motor 35 starts to run, by reason of the cam 7 again making bottom connection for approximately a thirty to forty second period (i.e. from the 256° point to the 259° point), so as to cause the pump to flush out the spray water from the tub 14 and direct it to the discharge line 30.

The cam 7 causes its switch element to go out of contact at the 259° point, and the cams 3 and 5 operate their switch elements to reverse the direction of the motor 35 back to its forward mode. During this time, the solenoid 316 remains energized so that water is continuing to run into the tub 14. When the 267° point is reached, the cam 8 moves its switch element to an open position to stop the timing motor 318 and permit the tub 14 to be completely filled with rinse water.

When sufficient water has flowed into the tub 14 so that the liquid level valve 314 moves to its up position, the valve 20 is closed, and power is again transmitted through line 320 to the main timer motor 318. The up connection of the switch of cam 1 continues to transmit power to the timer motor 318 until the 279° point is reached. During this time period, up to the 278° point the cam 7 has its switch in lower contact to cause the motor 35 to continue to agitate the basket 38, so that the basket is agitating during this time period while the tub 14 is filled with rinse water.

At the 277° point, the switch of cam 8 makes lower contact to insure that power continues to be transmitted to the timer motor 318 after the switch of cam 1 drops out at the 279° point.

At the 281° point, the switches of cam 3 and 5 again reverse, and at the 284° point the switch of cam 7 again makes lower contact so that the motor 35 begins turning in a reverse direction, so that the basket 38 continues to oscillate and the pump 22 pumps the rinse water from the tub 14. This continues until the 310° point (about four to five minutes). In the first two minutes or so, the tub 14 is completely emptied, and for the remaining time there is the "shake-dry" period, where the basket 38 continues to oscillate to shake off the excess rinse water.

After the 310° point, the cams rotate through to the 360° point, and repeat substantially the same rinsing process which took place from approximately the 260° point to the 310° point. Therefore, the cam action from the 310° to the 360° point will not be described herein.

When the cams reach the 360° point, the switch of cam 8 remains in bottom contact for another three degrees of travel (i.e. up to the 3° point) to cause the timer motor 318 to move to the 3° point. At the 360° point, the switch of cam 7 moves from its lower contact point to stop the motor 35 and moves into upper contact to cause current to be transmitted to the third indicator light 174. This indicates that the third final rinse cycle has been completed. This light 174 will remain on until the selector switch 12 is either disengaged or rotated to a different location.

Heating Circuit

Figure 14:
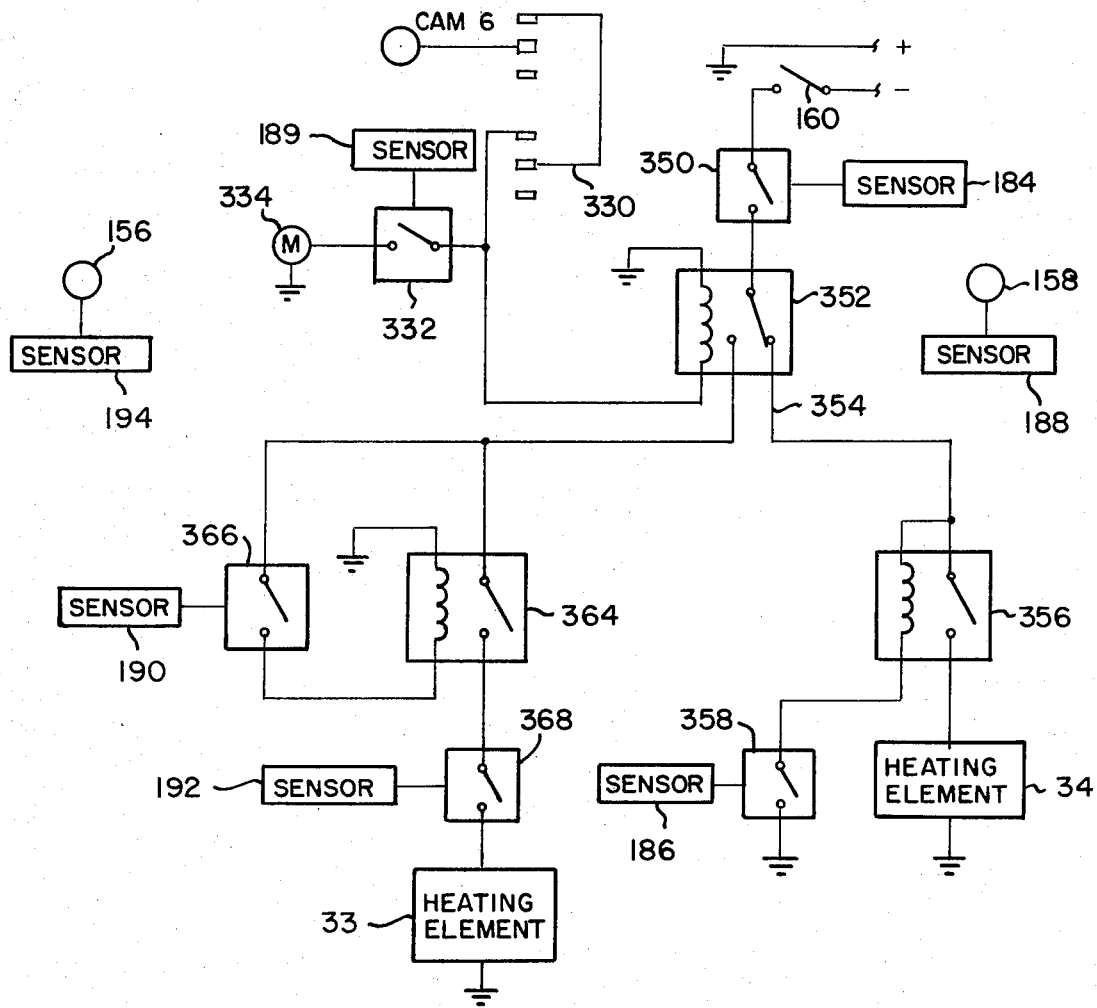
FIG. 14 is a diagram of the heating circuit of the present invention.

As described previously herein, when the second pasteurize/disinfect cycle is used, the heating switch 160 is pressed in to heat the liquid (either pasteurizing water or disinfectant liquid) to the desired temperature. During the second cycle, after the liquid has been transferred from tub 16 to tub 14, power is switched from the heating element 34 of the tub 16 to the heating element 33 of the tub 14. Also, the pasteurize/disinfect timer 154 is not activated until the liquid in the tub 14 is at or is brought to a predetermined temperature level. The circuitry by which this is accomplished is illustrated in FIG. 14. The components of FIG. 12 necessary for an understanding of the heating circuit are shown also in FIG. 14.

As indicated in FIG. 14, when the switch 160 is closed, current is transmitted to a thermostat 350 which is responsive to the sensor 184 on the tub 16. The thermostat 350 is a protective thermostat, which is normally closed and made responsive to the sensor 184 on the tub 16. When the temperature in the tub 16 reaches a predetermined level (i.e. 190°) the thermostat 350 opens and shuts off all current to the heating elements 33 and 34. The thermostat 350 can be manually reset to its closed position.

The line from the thermostat 350 connects to the switching element of a single pole double throw relay 352 which normally makes contact with a line 354 leading to a single pole single throw relay 356. This relay 356 in turn leads to the heating element 34 for the tub 16. The relay 356 is operated by a thermostat 358 which is in turn made responsive to a sensor 186. When the temperature in the tub 16 falls below a pre-determined level (e.g. 170° F.) the thermostat 358 closes to close the relay 356 and cause current to be transmitted to the heating element 334 to bring it to the desired temperature level. When this temperature level is reached, the thermostat 358 opens to in turn open the relay 356 and interrupt current to the heating element 34.

To describe the manner in which power is transferred from the heating element 34 to the heating element 33, as indicated previously herein, when the pasteurize/disinfect timer 154 is moved to a pre-determined timing position, this automatically moves switch 330 to its up position, as shown in both FIG. 12 and FIG. 14. At the 213° point in the timing cycle, cam 6 moves its switching element to the up position to transmit current through the switch 330 to the thermostat 332, which in turn communicates with the pasteurize/disinfect timer 334. The thermostat 332 is provided with the sensing element 189 which is responsive to temperature in the tub 14. When the temperature in the tub 14 reaches a predetermined level, the thermostat 332 closes to energize the timer motor 334 for the pasteurize/disinfect cycle.

Also, when the cam 6 moves to its up position to transmit current through the switch 330, the solenoid of the switch 352 is activated to cause the switch 352 to make contact with line 362 which in turn leads to a single pole single throw relay 364. This relay 364 is closed by a thermostat 366 which is in turn responsive to the temperature sensor 190 on the tub 14. When the temperature in the tub 14 drops below a predetermined level (e.g. 170° F.), the thermostat 366 closes to energize the coil of relay 364 and cause current to be transmitted through a protective thermostat 368 to the heating element 33. The protective thermostat 368 is normally closed, and is responsive to a sensor 192. When the sensor detects a temperature in the tub 14 above a predetermined level (e.g. 190° F.), the protective thermostat 368 opens to interrupt current to the heating element 33. This thermostat 368 can be manually reset to its closed position.

To review the operation of the heating circuit shown in FIG. 14, current is normally directed from switch 160 through the protective thermostat 350 (which is normally closed), through the switching relay 352, through the thermostat controlled relay 356, to the heating element 34. The thermostat 358 opens and closes to act through the relay 356 to interrupt and transmit current to the heating element 34 as needed to keep the liquid in the tub 16 at the desired temperature.

During the sequencing of the second pasteurize/disinfect cycle, (more specifically at the 213° point in the cycle), contact is made through the upper contact of cam 6 and switch 332 activate the switching relay 352 and cause power to be transmitted through line 362, then through relay 364, through the protective relay 368, to the heating element 33. The control thermostat 366 selectively closes and opens the relay 364 to energize and de-energize the heating element 330 to maintain the temperature in the tub 14 at the desired level.

In the event that during the transfer of the liquid from the tub 16 to the tub 14 the temperature of the liquid drops, the thermostat 332 for the pasteurize/disinfect timing motor 334 opens so that power is not transmitted to that motor 334. However, at such time as the liquid in the tub 14 does reach the desired level (by action of the heating element 33), the thermostat 332 closes to cause the motor 334 to operate and move the pasteurize/disinfect timer through its pre-set time period.

What is claimed is:

1. A washing apparatus, particularly adapted to clean elongate hollow articles, such as tubes and other equipment used in anesthetizing and inhalation therapy, said apparatus comprising:
   a. a housing structure,
   b. a tub mounted in said housing structure and adapted to contain a cleaning liquid,
   c. a container adapted to carry the articles which are to be cleaned, said container being mounted in said tub for rotation about a generally vertical axis of rotation,
   d. means to fill said tub with said cleaning liquid, e. means to empty said cleaning liquid from said tub,
f. power means operatively connected to said container to cause said container to oscillate angularly about said axis of rotation,
g. positioning means in said container arranged to engage and maintain said elongate articles in said container in circumferential alignment with the center of rotation of said container,
h. control means to cause said filling means to direct liquid into said tub, and also to cause said emptying means to remove said cleaning liquid from the tub, said control means further being arranged to activate said power means to oscillate said container during a time period when said tub is filled with said liquid to a cleaning level, and also to cause said power means to oscillate tub during a time period after cleaning liquid has been removed from said tub, whereby subsequent to cleaning liquid being removed from said tub, the articles in the container are oscillated angularly to remove at least a portion of liquid remaining on said articles after said tub is emptied of said cleaning liquid.

2. The apparatus as recited in claim 1, wherein said positioning means comprises at least one locating means positioned in said container, said locating means having vertically oriented and radially spaced partition means defining a plurality of circumferentially aligned, radially spaced locating areas to receive said articles in circumferential alignment.

3. The apparatus as recited in claim 2, wherein said locating means comprises at least one locating member having a base portion and a plurality of upstanding rod members, with adjacent rod members defining said locating areas.

4. The apparatus as recited in claim 1, wherein said positioning means comprises at least one clamping means, comprising a plurality of radially spaced clamping members, adapted to engage said articles, each of said clamping members defining a circumferentially aligned clamping area in which said articles are located to be clamped in circumferential alignment.

5. The apparatus as recited in claim 4, wherein said clamping means comprises a base member, and each of said clamping elements comprises a strap member connected to said base members and adapted to define a closed loop, within which the strap member receives the articles and engages said articles in clamping engagement.

6. The apparatus as recited in claim 1, wherein said container has at least one horizontal partition member dividing said container into an upper section and a lower section, said positioning means being located in said lower section so that the difficult to clean elongate articles are located in said lower section, and other articles to be cleaned are able to be placed in said upper section.

7. The apparatus as recited in claim 6, wherein said control means is so arranged to cause said power means to oscillate said container during a time period when said filling means is directing cleaning liquid into said tub, in a manner that when said tub is partially filled with cleaning liquid, the container is oscillating in said tub to cause a cleaning action of the articles in the lower section of the container.

8. The apparatus as recited in claim 6, wherein said control means is arranged to cause said power means to oscillate said container during a period when said emptying means is emptying the cleaning liquid from the tub, in a manner that during the time period when emptying of the tub begins to a time when emptying of said tub is partially completed, said container is caused to oscillate to impart a cleaning action to the articles in the lower section of the container.

9. The apparatus as recited in claim 1, wherein:
a. said container has at least one horizontal partition member dividing said container into an upper section and a lower section, said positioning means being located in said lower section so that the difficult to clean elongate articles are located in said lower section, and other articles to be cleaned are able to be placed in said upper section;
b. said control means is so arranged to cause said power means to oscillate said container during a time period when said filling means is directing cleaning liquid into said tub, in a manner that when said tub is partially filled with cleaning liquid, the container is oscillating in said tub to cause a cleaning action of the articles in the lower section of the container;
c. said control means is also arranged to cause said power means to oscillate said container during a period when said emptying means is emptying the cleaning liquid from the tub, in a manner that during the time period when emptying of the tub begins to a time when emptying of said tub is partially completed, said container is caused to oscillate to impart a cleaning action to the articles in the lower section of the container.

10. A cleaning apparatus adapted to clean articles by means of a cleaning liquid, said apparatus comprising:
a. a housing structure,
b. a tub to contain said cleaning liquid,
c. a container adapted to carry the articles to be cleaned, said container being mounted in said tub for rotation about a generally vertical axis of rotation,
d. filling means to direct said cleaning liquid into said tub,
e. motor means operatively connected to said container to oscillate said container angularly about said axis of rotation,
f. pump means to direct said cleaning liquid from said tub,
g. control means to activate said motor means to cause said container to oscillate, and simultaneously to activate one of said filling means and pump means so as to cause said container to oscillate during a period where said tub is partially filled with cleaning fluid.

11. The apparatus as recited in claim 10, wherein said control means is arranged to activate said motor means and said filling means simultaneously, so that said container is oscillating while said tub is being filled with cleaning liquid.

12. The apparatus as recited in claim 10, wherein said control means is arranged to oscillate said container and simultaneously activate said pump means so that said container is caused to oscillate while said pump means is emptying the tub of cleaning liquid.

13. The apparatus as recited in claim 12, wherein:
a. said motor means has a forward operating mode, and a reverse operating mode,
b. said apparatus comprising a first transmission operatively connected between said motor means and said container, said first transmission being arranged to translate rotary motion of said motor means in both its forward and reverse operating mode to oscillating motion, whereby said container is caused to oscillate when said motor means is operating in either its forward mode or reverse mode, c. second transmission operatively connected between said motor means and said pump means, said motor means causing said pump means to operate in a pump in direction when said motor is operating in its forward mode, and to cause said pump means to operate in a pump out direction when said motor means is operating in its reverse mode, d. said control means being arranged to operate said motor means in its forward mode during a cleaning period after said tub has been filled with cleaning liquid, and to operate said motor means in its reverse mode during an emptying period subsequent to said cleaning period, so that said container continues to oscillate as the pump means is emptying said tub of said cleaning liquid.

14. A cleaning apparatus adapted to clean with a cleaning liquid articles to which said liquid adheres as a surface liquid, said apparatus comprising:
    a. a housing structure,
    b. a tub to contain a cleaning liquid,
    c. a container adapted to carry the articles to be cleaned, said container being mounted in said tub for rotation about a generally vertical axis of rotation,
    d. filling means to direct said cleaning liquid into said tub,
    e. motor means operatively connected to said container to oscillate said container angularly about said axis of rotation, said motor means having a forward operating mode and a reverse operating mode,
    f. pump means to direct said cleaning liquid from said tub,
    g. a first transmission means operatively connected between said motor means and said container, said transmission means being arranged to translate rotary motion of said motor means in both its forward and reverse mode to oscillating motion, whereby said container is caused to oscillate when said motor means is operating in either its forward mode or reverse mode,
    h. second transmission means operatively connected between the motor means and the pump means, said motor means causing said pump means to operate in a pump in direction when said motor is operating in its forward mode, and to cause said pump to operate in a pump out direction when said motor means is operating in its reverse mode,
    i. control means comprising:
        1. cam means arranged to travel through an operating cycle,
        2. a timer motor to move said cam means through its operating cycle,
        3. motor reversing switch means to cause said motor means to be in its forward mode or reverse mode,
        4. motor power switch means to supply power to said motor,
        5. liquid level switch means responsive to level of cleaning liquid in said tub, said liquid level switch means having a first low level position, where said switch means activates said filling means and said motor power switch means simultaneously, and a second high level position where said liquid level switch means deactivates said filling means and activates said timer motor to cause said cam means to travel in its operating cycle,
        6. said cam means having a wash position where said cam means acts through said motor reversing switch means and said motor power switch means to cause said motor means to operate in its forward mode to oscillate said container and to cause said pump means to operate in said pump in mode,
        7. said cam means also having an emptying position, where said cam means activates said motor reverse switch means and said motor power switch means to cause said motor means to operate in its reverse mode and thus pump out cleaning liquid from said tub while said motor means is causing said container to oscillate,
        8. said cam means having a shake-dry position, where said motor power switch means is activated to cause said container to oscillate subsequent to said pump means pumping out the cleaning liquid from said tub.

15. The apparatus as recited in claim 14, further comprising:
    a. a transfer tub to contain a second liquid medium, adapted to sterilize the articles being cleaned,
    b. first heating means arranged to heat liquid in said transfer tub,
    c. second heating means to heat liquid in said first named tub,
    d. diverter valve means connected to said pump means, said diverter valve means having a first position where flow from said pump means is to a discharge outlet, and a second position where flow to and from said pump means is to and from said transfer tub,
    e. said control means comprising diverter valve switch means to move said diverter valve means to its second position, said control means further being arranged to drive said motor means in its forward mode subsequent to moving the diverter valve to its second position, so as to pump said second liquid into said first named tub while causing said container to oscillate,
    f. heat switch means to transfer power from said first heating means to said second heating means, said control means being arranged to cause said heat switch means to operate when said second liquid is transferred to said first named tub.

16. The apparatus as recited in claim 15, further comprising a second timing means to determine a time period during which said second liquid is to remain in said first named tub, said apparatus further comprising a thermostat means responsive to temperature in said first named tub, said thermostat means being arranged to initiate action of said second timing means only after said thermostat senses a predetermined temperature level in said first named tub.

17. The apparatus as recited in claim 16, further comprising a second liquid level switch means responsive to liquid level in said first named tub, said second liquid level switch means being arranged to activate said second timing means with said thermostat means, in a manner that said second timing means is not activated until liquid level in said first named tub has reached a predetermined full level.

18. A washing apparatus, particularly adapted to clean elongate hollow articles, such as tubes and other equipment used in anesthetizing and inhalation therapy, said apparatus comprising:
 a. a housing structure,
 b. a tub mounted in said housing structure and adapted to contain a cleaning liquid,
 c. a container adapted to carry the articles which are to be cleaned, said container being mounted in said tub for rotation about a generally vertical axis of rotation,
 d. means to fill said tub with said cleaning liquid,
 e. means to empty said cleaning liquid from said tub,
 f. power means operatively connected to said container to cause said container to oscillate angularly about said axis of rotation,
 g. positioning means in said container arranged to engage and maintain said elongate articles in said container in circumferential alignment with the center of rotation of said container,
 h. control means to cause said filling means to direct liquid into said tub, and also to cause said emptying means to remove said cleaning liquid from the tub, said control means further being arranged to activate said power means to oscillate said container during a time period when said tub is filled with said liquid to a cleaning level, and also to cause said power means to oscillate the tub during a time period after cleaning liquid has been removed from said tub,
 i. said positioning means comprising at least one locating means positioned in said container, said locating means having vertically oriented and radially spaced partition means defining a plurality of circumferentially aligned, radially spaced locating areas to receive said articles in circumferential alignment;
 j. said positioning means further comprising at least one clamping means, comprising clamping members, adapted to engage said articles, each of said clamping members defining a circumferentially aligned clamping area in which said articles are located to be clamped in circumferential alignment, whereby subsequent to cleaning liquid being removed from said tub, the articles in the container are oscillated angularly to remove at least a portion of liquid remaining on said articles after said tub is emptied of said cleaning liquid.

19. The apparatus as recited in claim 18, wherein:
 a. said locating means comprises at least one locating member having a base portion and a plurality of upstanding rod members, with adjacent rod members defining said locating areas;
 b. said clamping means comprises a base member, and each of said clamping elements comprises a strap member connected to said clamping element and adapted to define a closed loop, within which the strap member receives the articles and engages said articles in clamping engagement.

20. A washing apparatus, particularly adapted to clean elongate hollow articles, such as tubes and other equipment used in anesthetizing and inhalation therapy, said apparatus comprising:
 a. a housing structure,
 b. a tub mounted in said housing structure and adapted to contain a cleaning liquid,
 c. a container adapted to carry the articles which are to be cleaned, said container being mounted in said tub for rotation about a generally vertical axis of rotation,
 d. means to fill said tub with said cleaning liquid,
 e. means to empty said cleaning liquid from said tub,
 f. power means operatively connected to said container to cause said container to oscillate angularly about said axis of rotation,
 g. positioning means in said container arranged to engage and maintain said elongate articles in said container in circumferential alignment with the center of rotation of said container,
 h. control means to cause said filling means to direct liquid into said tub, and also to cause said emptying means to remove said cleaning liquid from the tub, said control means further being arranged to activate said power means to oscillate said container during a time period when said tub is filled with said liquid to a cleaning level, and also to cause said power means to oscillate the tub during a time period after cleaning liquid has been removed from said tub,
 i. said container having a horizontal partition member to separate said container into upper and lower sections, said partition member comprising a plate and a resilient wire member positioned at a pheripheral portion of said plate, said container having a plurality of vertically spaced groove means to receive said wire member, in a manner that said wire member can be sprung inwardly to provide clearance for the partition member to be placed in said container, and sprung outwardly to engage selected groove means to locate the partition member at a desired vertical location,
whereby subsequent to cleaning liquid being removed from said tub, the articles in the container are oscillated angularly to remove at least a portion of liquid remaining on said articles after said tub is emptied of said cleaning liquid.

21. The apparatus as recited in claim 20, wherein said wire member has a plurality of brackets connecting said wire member to said plate, with said brackets being movable relative to said plate, whereby said wire member can be sprung inwardly and outwardly while said brackets maintain engagement with said plate.

22. The apparatus as recited in claim 21, wherein said plate is provided with a plurality of grooves, each groove arranged to accommodate a related one of said brackets as said wire member is sprung inwardly.

23. The apparatus as recited in claim 20, wherein said wire member has a peripheral portion extending circumferentially around said plate, and two radially inwardly extending arm portions, said arm portions being spaced moderately from one another, so that said arm portions can be grasped and pulled toward each other to cause said wire member to be sprung inwardly.

24. The apparatus as recited in claim 23, wherein said arm portions of the wire member are positioned below said plate, said plate being provided with a generally circumferentially aligned slot extending beyond said arm members, so that access through said slot can be obtained to grasp said arm members to move said arm members toward one another.

25. A washing apparatus, particularly adapted to clean elongate hollow articles, such as tubes and other equipment used in anesthetizing and inhalation therapy, said apparatus comprising:

a. a housing structure,
b. a tub mounted in said housing structure and adapted to contain a cleaning liquid,
c. a container adapted to carry the articles which are to be cleaned, said container being mounted in said tub for rotation about a generally vertical axis of rotation,
d. means to fill said tub with said cleaning liquid,
e. means to empty said cleaning liquid from said tub,
f. power means operatively connected to said container to cause said container to oscillate angularly about said axis of rotation,
g. positioning means in said container arranged to engage and maintain said elongate articles in said container in circumferential alignment with the center of rotation of said container,
h. control means to cause said filling means to direct liquid into said tub, and also to cause said emptying means to remove said cleaning liquid from the tub, said control means further being arranged to activate said power means to oscillate said container during a time period when said tub is filled with said liquid to a cleaning level, and also to cause said power means to oscillate tub during a time period after cleaning liquid has been removed from said tub,
i. said container having a horizontal partition member to separate said container into upper and lower sections, said partition member comprising a plate and a resilient wire member positioned at a peripheral portion of said plate, said container having a plurality of vertically spaced groove means to receive said wire member, in a manner that said wire member can be sprung inwardly to provide clearance for partition member to be placed in said container, and sprung outwardly to engage selected groove means to locate the partition member at a desired vertical location;
j. said wire member having a plurality of brackets connecting said wire member to said plate, with said brackets being movable relative to said plate, whereby said wire member can be sprung inwardly and outwardly while said brackets maintain engagement with said plate;
k. said plate being provided with a plurality of grooves, each groove arranged to accommodate a related one of said brackets as said wire member is sprung inwardly;
l. said wire member having a peripheral portion extending circumferentially around said plate, and two radially inwardly extending arm portions, said arm portions being spaced moderately from one another, so that said arm portions can be grasped and pulled toward each other to cause said wire member to be sprung inwardly;
m. said arm portions of the wire member being positioned below said plate, said plate being provided with a generally circumferentially aligned slot extending beyond said arm members, so that access through said slot can be obtained to grasp said arm members to move said arm members toward one another, whereby subsequent to cleaning liquid being removed from said tub, the articles in the container are oscillated angularly to remove at least a portion of liquid remaining on said articles after said tub is emptied of said cleaning liquid.

26. A washing apparatus, particularly adapted to clean elongate hollow articles, such as tubes and other equipment used in anesthetizing and inhalation therapy, said apparatus comprising:
a. a housing structure,
b. a tub mounted in said housing structure and adapted to contain a cleaning liquid,
c. a container adapted to carry the articles which are to be cleaned, said container being mounted in said tub for rotation about a generally vertical axis of rotation,
d. means to fill said tub with said cleaning liquid,
e. means to empty said cleaning liquid from said tub,
f. power means operatively connected to said container to cause said container to oscillate angularly about said axis of rotation,
g. positioning means in said container arranged to engage and maintain said elongate articles in said container in circumferential alignment with the center of rotation of said container,
h. control means to cause said filling means to direct liquid into said tub, and also to cause said emptying means to remove said cleaning liquid from the tub, said control means further being arranged to activate said power means to oscillate said container during a time period when said tub is filled with said liquid to a cleaning level, and also to cause said power means to oscillate tub during a time period after cleaning liquid has been removed from said tub,
i. said positioning means comprising at least one locating means having vertically oriented and radially spaced partition means defining a plurality of circumferentially aligned, radially spaced locating areas to receive said articles in circumferential alignment;
j. said positioning means further comprising at least one clamping means, comprising a plurality of radially spaced clamping members, adapted to engage said articles, each of said clamping members defining a circumferentially aligned clamping area in which said articles are located to be clamped in circumferential alignment;
k. said container having at least one horizontal partition member dividing said container into an upper section and a lower section, said positioning means being located in said lower section so that the difficult to clean elongate articles are located in said lower section, and other articles to be cleaned are able to be placed in said upper section, whereby subsequent to cleaning liquid being removed from said tub, the articles in the container are oscillated angularly to remove at least a portion of liquid remaining on said articles after said tub is emptied of said cleaning liquid.

27. The apparatus as recited in claim 26, wherein said control means is so arranged to cause said power means to oscillate said container during a time period when said filling means is directing cleaning liquid into said tub, in a manner that when said tub is partially filled with cleaning liquid, the container is oscillating in said tub to cause a cleaning action of the articles in the lower section of the container.

28. The apparatus as recited in claim 26 wherein said control means is arranged to cause said power means to oscillate said container during a period when said emptying means is emptying the cleaning liquid from the tub, in a manner that during the time period when emptying of the tub begins to a time when emptying of said tub is partially completed, said container is caused to oscillate to impart a cleaning action to the articles in the lower section of the container.

29. The apparatus as recited in claim 26, wherein:
   a. said control means is so arranged to cause said power means to oscillate said container during a time period when said filling means is directing cleaning liquid into said tub, in a manner that when said tub is partially filled with cleaning liquid, the container is oscillating in said tub to cause a cleaning action of the articles in the lower section of the container;
   b. said control means is also arranged to cause said power means to oscillate said container during a period when said emptying means is emptying the cleaning liquid from the tub, in a manner that during the time period when emptying of the tub begins to a time when emptying of said tub is partially completed, said container is caused to oscillate to impart a cleaning action to the articles in the lower section of the container.

30. A washing apparatus, particularly adapted to clean elongate hollow articles, such as tubes and other equipment used in anesthetizing and inhalation therapy, said apparatus comprising:
   a. a housing structure,
   b. a tub mounted in said housing structure and adapted to contain a cleaning liquid,
   c. a container adapted to carry the articles which are to be cleaned, said container being mounted in said tub for rotation about a generally vertical axis of rotation,
   d. means to fill said tub with said cleaning liquid,
   e. means to empty said cleaning liquid from said tub,
   f. power means operatively connected to said container to cause said container to oscillate angularly about said axis of rotation,
   g. positioning means in said container arranged to engage and maintain said elongate articles in said container in circumferential alignment with the center of rotation of said container,
   h. control means to cause said filling means to direct liquid into said tub, and also to cause said emptying means to remove said cleaning liquid from the tub, said control means further being arranged to activate said power means to oscillate said container during a time period when said tub is filled with said liquid to a cleaning level, and also to cause said power means to oscillate tub during a time period after cleaning liquid has been removed from said tub,
   i. said positioning means comprising at least one locating means positioned in said basket, said locating means having vertically oriented and radially spaced partition means defining a plurality of circumferentially aligned, radially spaced locating areas to receive said articles in circumferential alignment;
   j. said positioning means further comprising at least one clamping means, comprising a plurality of radially spaced clamping members, adapted to engage said articles, each of said clamping members defining a circumferentially aligned clamping area in which said articles are located to be clamped in circumferential alignment;
   k. said container having at least one horizontal partition member dividing said container into an upper section and a lower section, said positioning means being located in said lower section so that the difficult to clean elongate articles are located in said lower section, and other articles to be cleaned are able to be placed in said upper section.
   l. said horizontal partition member comprising a plate and a resilient wire member positioned at a peripheral portion of said plate, said container having a plurality of vertically spaced groove means to receive said wire member, in a manner that said wire member can be sprung inwardly to provide clearance for the partition member to be placed in said container, and sprung outwardly to engage selected groove means to locate the partition member at a desired vertical location, whereby subsequent to cleaning liquid being removed from said tub, the articles in the container are oscillated angularly to remove at least a portion of liquid remaining on said articles after said tub is emptied of said cleaning liquid.

31. A washing apparatus, particularly adapted to clean elongate hollow articles, such as tubes and other equipment used in anesthetizing and inhalation therapy, said apparatus comprising:
   a. a housing structure,
   b. a tub mounted in said housing structure and adapted to contain a cleaning liquid,
   c. a container adapted to carry the articles which are to be cleaned, said container being mounted in said tub for rotation about a generally vertical axis of rotation,
   d. means to fill said tub with said cleaning liquid,
   e. means to empty said cleaning liquid from said tub,
   f. power means operatively connected to said container to cause said container to oscillate angularly about said axis of rotation,
   g. positioning means in said container arranged to engage and maintain said elongate articles in said container in circumferential alignment with the center of rotation of said container,
   h. control means to cause said filling means to direct liquid into said tub, and also to cause said emptying means to remove said cleaning liquid from the tub, said control means further being arranged to activate said power means to oscillate said container during a time period when said tub is filled with said liquid to a cleaning level, and also to cause said power means to oscillate tub during a time period after cleaning liquid has been removed from said tub,
   i. said container having a hub portion and a peripheral portion, said container also having a plurality of interior vertical mounting posts at said hub portion, and a plurality of outer circumferential posts at said peripheral portion, pairs of inner and outer posts being radially aligned with one another;
   j. said positioning means comprising at least one positioning member having a horizontally extending base portion and two end arm portions, each of said arm portions being adapted to engage a related one of said posts in mounting engagement, whereby said positioning member can be radially aligned in said container by one of said arm members engaging an inner post, and the other of said arm members engaging an outer post, whereby subsequent to cleaning liquid being removed from said tub, the articles in the container are oscillated angularly to remove at least a portion of liquid remaining on said articles after said tub is emptied of said cleaning liquid.

32. The apparatus as recited in claim 31, wherein said positioning member further comprises a plurality of upstanding rod members, with adjacent rod members defining locating areas.

33. The apparatus as recited in claim 31, wherein said positioning member comprises a plurality of radially spaced clamping members, each adapted to engage said articles, each of said clamping members defining a circumferentially aligned clamping area in which said articles are located to be clamped in said circumferential alignment.

34. A washing apparatus, particularly adapted to clean elongate hollow articles, such as tubes and other equipment used in anesthetizing and inhalation therapy, said apparatus comprising:
   a. a housing structure,
   b. a tub mounted in said housing structure and adapted to contain a cleaning liquid,
   c. a container adapted to carry the articles which are to be cleaned, said container being mounted in said tub for rotation about a generally vertical axis of rotation,
   d. means to fill said tub with said cleaning liquid,
   e. means to empty said cleaning liquid from said tub,
   f. power means operatively connected to said container to cause said container to oscillate angularly about said axis of rotation,
   g. positioning means in said container arranged to engage and maintain said elongate articles in said container in circumferential alignment with the center of rotation of said container,
   h. control means to cause said filling means to direct liquid into said tub, and also to cause said emptying means to remove said cleaning liquid from the tub, said control means further being arranged to activate said power means to oscillate said container during a time period when said tub is filled with said liquid to a cleaning level, and also to cause said power means to oscillate the tub during a time period after cleaning liquid has been removed from said tub,
   i. said container having a hub portion and a peripheral portion, said container also having a plurality of interior vertical mounting posts at said hub portion, and a plurality of outer circumferential posts at said peripheral portion, pairs of inner and outer posts being radially aligned with one another,
   j. said apparatus further comprising at least one locating member positioned in said basket, said locating member having a horizontally extending base portion and two end arm portions, each of said arm portions being adapted to engage a related one of said posts in mounting engagement, whereby said locating member can be radially aligned in said basket by one of said arm members engaging an inner post, and the other of said arm members engaging an outer post, said locating member further comprising a plurality of upstanding rod members with adjacent rod members defining locating areas,
   k. said apparatus further comprising at least one clamping means having a second horizontally extending base portion and two second end arm portions, each of said second arm portions being adapted to engage a related one of said posts in mounting engagement, whereby said clamping means can be radially aligned in said basket by one of said second arm portions engaging an outer post, said clamping means having a plurality of radially spaced clamping members, adapted to engage said articles, each of said clamping members defining a circumferentially aligned clamping area in which said articles are located to be clamped in circumferential alignment, whereby subsequent to cleaning liquid being removed from said tub, the articles in the container are oscillated angularly to remove at least a portion of liquid remaining on said articles after said tub is emptied of said cleaning liquid.

35. A washing apparatus, particularly adapted to clean elongate hollow articles, such as tubes and other equipment used in anesthetizing and inhalation therapy, said apparatus comprising:
   a. a housing structure,
   b. a tub mounted in said housing structure and adapted to contain a cleaning liquid,
   c. a container adapted to carry the articles which are to be cleaned, said container being mounted in said tub for rotation about a generally vertical axis of rotation,
   d. means to fill said tub with said cleaning liquid,
   e. means to empty said cleaning liquid from said tub,
   f. power means operatively connected to said container to cause said container to oscillate angularly about said axis of rotation,
   g. positioning means in said container arranged to engage and maintain said elongate articles in said container in circumferential alignment with the center of rotation of said container,
   h. control means to cause said filling means to direct liquid into said tub, and also to cause said emptying means to remove said cleaning liquid from the tub, said control means further being arranged to activate said power means to oscillate said container during a time period when said tub is filled with said liquid to a cleaning level, and also to cause said power means to oscillate tub during a time period after cleaning liquid has been removed from said tub,
   i. said container having a horizontal partition member to separate said container into upper and lower sections, said partition member comprising a plate and a resilient wire member positioned at a peripheral portion of said plate, said container having a plurality of vertically spaced groove means to receive said wire member, in a manner that said wire member can be sprung inwardly to provide clearance for partition member to be placed in said container, and sprung outwardly to engage selected groove means to locate the partition member at a desired vertical location;
   j. said container having a hub portion and a peripheral portion, said container also having a plurality of interior vertical mounting posts at said hub portion, and a plurality of outer circumferential posts at said peripheral portion, pairs of inner and outer posts being radially aligned with one another;
   k. said positioning means comprising at least one positioning member having a horizontally extending base portion and two end arm portions, each of said arm portions being adapted to engage a related one of said posts in mounting engagement, whereby said positioning member can be radially aligned in said container by one of said arm members engaging an inner posts, and the other of said arm members engaging an outer post;

l. said groove means comprising a plurality of horizontally aligned grooves formed in said outer posts, whereby subsequent to cleaning liquid being removed from said tub, the articles in the container are oscillated angularly to remove at least a portion of liquid remaining on said articles after said tub is emptied of said cleaning liquid.

36. The apparatus as recited in claim 35, further comprising a plurality of vertical partition members, each of which has lateral vertical edge portions adapted to engage a pair of inner and outer posts, whereby with said horizontal partition member in place, said radial partition members are able to separate the upper section of the container into circumferentially spaced compartments to contain other articles to be cleaned.

37. A washing apparatus, particularly adapted to clean elongate hollow articles, such as tubes and other equipment used in anesthetizing and inhalation therapy, said apparatus comprising:
  a. a housing structure,
  b. a tub mounted in said housing structure and adapted to contain a cleaning liquid,
  c. a container adapted to carry the articles which are to be cleaned, said container being mounted in said tub for rotation about a generally vertical axis of rotation,
  d. means to fill said tub with said cleaning liquid,
  e. means to empty said cleaning liquid from said tub,
  f. power means operatively connected to said container to cause said container to oscillate angularly about said axis of rotation,
  g. positioning means in said container arranged to engage and maintain said elongate articles in said container in circumferential alignment with the center of rotation of said container,
  h. control means to cause said filling means to direct liquid into said tub, and also to cause said emptying means to remove said cleaning liquid from the tub, said control means further being arranged to activate said power means to oscillate said container during a time period when said tub is filled with said liquid to a cleaning level, and also to cause said power means to oscillate tub during a time period after cleaning liquid has been removed from said tub,
  i. said positioning means comprising a least one locating means positioned in said container, said locating means having vertically oriented and radially spaced partition means defining a plurality of circumferentially aligned, radially spaced locating areas to receive said articles in circumferential alignment,
  j. said positioning means further comprising at least one clamping means, comprising a plurality of radially spaced clamping members, adapted to engage said articles, each of said clamping members defining a circumferentially aligned clamping area in which said articles are located to be clamped in circumferential alignment,
  k. said container having at least one horizontal partition member dividing said container into an upper section and a lower section, said positioning means being located in said lower section so that the difficult to clean elongate articles are located in said lower section, and other articles to be cleaned are able to be placed in said upper section,
  l. said control means being so arranged to cause said power means to oscillate said container during a time period when said filling means is directing cleaning liquid into said tub, in a manner that when said tub is partially filled with cleaning liquid, the container is oscillated in said tub to cause a cleaning action of the articles in the lower section of the container,
  m. said control means being also arranged to cause said power means to oscillate said container during a period when said emptying means is emptying the cleaning liquid from said tub, in a manner that during the time period when emptying of said tub is partially completed, the container is caused to oscillate to impart a cleaning action to the articles in the lower section of the container,
  n. said partition member comprising a plate and a resilient wire member positioned at a peripheral portion of said plate, said container having a plurality of vertically spaced groove means to receive said wire member, in a manner that said wire member can be sprung inwardly to provide clearance for the partition member to be placed in the container, and sprung outwardly to engage selected groove means to locate the partition member at a desired vertical location,
  o. said container having a hub portion and a peripheral portion, said container also having a plurality of interior vertical mounting posts at said hub portion, and a plurality of outer circumferential posts at said peripheral portion, pairs of inner and outer posts being radially aligned with one another,
  p. said locating means and said clamping means each comprising a base portion and two end arm portions, each of said arm portions being adapted to engage a related one of said posts in mounting engagement, whereby each of said locating means and clamping means can be radially aligned in said container by one of said arm members engaging an inner post and the other of said arm members engaging an outer post,
  q. said groove means comprising a plurality of horizontally aligned grooves formed in said outer posts, whereby subsequent to cleaning liquid being removed from said tub, the articles in the container are oscillated angularly to remove at least a portion of liquid remaining on said articles after said tub is emptied of said cleaning liquid.

38. The apparatus as recited in claim 37, wherein:
  a. said locating means comprises at least one locating member having a plurality of upstanding rod members, with adjacent rod members defining locating areas,
  b. said clamping means having its clamping members each comprising a strap member connected to the base member and adapted to define a closed loop, within which the strap member receives the articles and engages said articles in clamping engagement,
  c. said wire member has a plurality of brackets connecting said wire member to said plate, with said brackets being movable relative to said plate, whereby said wire member can be sprung inwardly and outwardly while said brackets maintain engagement with said plate, d. said plate being provided with a plurality of grooves, each groove arranged to accomodate a related one of said brackets as said wire member is sprung inwardly, e. said wire member having a peripheral portion extending circumferentially around said plate, and two radially inwardly extending arm portions, said arm portions being spaced moderately from one another, so that the arm portions can be grasped and pulled toward each other to cause said wire member to be sprung inwardly, f. said arm portions of the wire member being positioned below said plate, said plate being provided with a generally circumferentially aligned slot extending beyond said arm members so that access through said slot can be obtained to grasp said arm members to move said arm members toward one another.

39. A cleaning apparatus adapted to clean articles by means of a cleaning liquid, said apparatus comprising:
a. a housing structure,
b. a tub to contain said cleaning liquid,
c. a container adapted to carry the articles to be cleaned, said container being mounted in said tub for rotation about a generally vertical axis of rotation,
d. filling means to direct said cleaning liquid into said tub,
e. motor means operatively connected to said container to oscillate said container angularly about said axis of rotation,
f. pump means to direct said cleaning liquid from said tub,
g. control means to activate said motor means to cause said container to oscillate, and simultaneously to activate one of said filling means and pump means so as to cause said container to oscillate during a period where said tub is partially filled with cleaning fluid,
h. said control means being arranged to activate said motor means and said filling means simultaneously, so that said container is oscillating while said tub is being filled with cleaning liquid,
i. a liquid level switch means operatively connected to said tub in such a manner to be responsive to a level of cleaning liquid in said tub, said liquid level switch means having a first low level position, where said switch means activates said filling means and said motor means simultaneously, and a second high level position where said liquid level switch means deactivates said filling means,
j. said control means further comprising a timer motor, arranged to operate said motor means through a washing period,
k. said liquid level switch means being operatively connected to said timer motor to activate said timer motor at its high level position, and thus operate said motor means through said washing period.

40. A cleaning apparatus adapted to clean articles by means of a cleaning liquid, said apparatus comprising:
a. a housing structure,
b. a tub to contain said cleaning liquid,
c. a container adapted to carry the articles to be cleaned, said container being mounted in said tub for rotation about a generally vertical axis of rotation,
d. filling means to direct said cleaning liquid into said tub,
e. motor means operatively connected to said container to oscillate said container angularly about said axis of rotation,
f. pump means to direct said cleaning liquid from said tub,
g. control means to activate said motor means to cause said container to oscillate, and simultaneously to activate one of said filling means and pump means so as to cause said container to oscillate during a period where said tub is partially filled with cleaning fluid,
h. a liquid level switch means being operatively connected to said tub in such a manner to be responsive to a level of cleaning liquid in said tub, said liquid level switch means having a first low level position, where said switch means activates said filling means and said motor means simultaneously, and a second high level position where said liquid level switch means deactivates said filling means,
i. said control means further comprising a timer motor, arranged to operate said motor means through a washing period,
j. said liquid level switch means being operatively connected to said timer motor to activate said timer motor at its high level position, and thus operate said motor means through said washing period,
k. said motor having a forward operating mode, and a reverse operating mode,
l. said apparatus comprising a first transmission operatively connected between said motor means and said container, said transmission being arranged to translate rotary motion of said motor in both its forward and reverse operating mode to oscillating motion, whereby said container is caused to oscillate when said motor means is operating in either its foward mode or reverse mode,
m. second transmission means operatively connected between said motor means and said pump means, said motor means causing said pump means to operate in a pump in direction when said motor means is operating in its forward mode, and to cause said pump means to operate in a pump out direction when said motor means is operating in its reverse mode,
n. said control means being arranged to operate said motor means in its forward mode during a cleaning period after said tub has been filled with cleaning liquid, and to operate said motor means in its reverse mode during an emptying period subsequent to said cleaning period, so that said container continues to oscillate as the pump means is emptying said tub of said cleaning liquid.

* * * * *